United States Patent [19]
Yabe et al.

[11] Patent Number: 5,575,752
[45] Date of Patent: Nov. 19, 1996

[54] ENDOSCOPE SYSTEM, COVER TYPE ENDOSCOPE UNIT, CHANNELED COVER TYPE ENDOSCOPE UNIT, HOLDING TOOL IN ENDOSCOPE SYSTEM, AND HOUSING MEMBER OF COVER TYPE ENDOSCOPE UNIT

[75] Inventors: Hisao Yabe; Akira Suzuki; Minoru Yamazaki; Hideo Ito, all of Hachioji; Yoshihiro Iida, Tama; Yoshio Tashiro, Hino; Osamu Tamada; Hiroshi Ishii, both of Hachioji, all of Japan

[73] Assignee: Olympus Optical Co., Ltd., Tokyo, Japan

[21] Appl. No.: 37,283

[22] Filed: Mar. 26, 1993

[30] Foreign Application Priority Data

Feb. 19, 1993 [JP] Japan .................. 5-005603 U
Feb. 19, 1993 [JP] Japan .................. 5-005604 U
Feb. 22, 1993 [JP] Japan .................. 5-005926 U

[51] Int. Cl.$^6$ ................................ A61B 1/04
[52] U.S. Cl. ................. 600/121; 600/123; 600/122
[58] Field of Search ............... 128/4, 6; 359/823, 359/703; 600/121, 122, 123, 124, 125

[56] References Cited

U.S. PATENT DOCUMENTS

| | | | |
|---|---|---|---|
| Re. 34,110 | 9/1992 | Opie . | |
| 3,162,190 | 12/1964 | Del Gizzo . | |
| 4,646,722 | 3/1987 | Silverstein | 128/4 |
| 4,721,097 | 1/1988 | D'Amelio | 128/4 |
| 4,741,326 | 5/1988 | Sidall | 128/4 |
| 4,825,850 | 5/1989 | Opie | 128/4 |
| 4,869,238 | 9/1989 | Opie | 128/6 |
| 4,878,485 | 11/1989 | Adair | 128/6 |
| 4,886,049 | 12/1989 | Darras | 128/4 |
| 4,907,395 | 3/1990 | Opie | 53/434 |
| 4,991,564 | 2/1991 | Takahashi | 128/4 |
| 4,991,565 | 2/1991 | Takahashi | 128/4 |
| 4,997,084 | 3/1991 | Opie | 206/364 |
| 5,050,585 | 9/1991 | Takahashi | 128/4 |
| 5,058,567 | 10/1991 | Takahashi | 128/4 |
| 5,078,503 | 1/1992 | Ueda | 359/823 |

FOREIGN PATENT DOCUMENTS

| | | |
|---|---|---|
| 0184778 | 6/1986 | European Pat. Off. . |
| 0310515 | 4/1989 | European Pat. Off. . |
| 0338567 | 10/1989 | European Pat. Off. . |
| 0341718 | 11/1989 | European Pat. Off. . |
| 0341719 | 11/1989 | European Pat. Off. . |
| 0349479 | 1/1990 | European Pat. Off. . |
| 0440252 | 8/1991 | European Pat. Off. . |
| 0440254 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |
| 2-57228 | 2/1990 | Japan . |
| 2-54734 | 11/1990 | Japan . |
| 3-29634 | 2/1991 | Japan . |
| 3-29635 | 2/1991 | Japan . |
| 3-37029 | 2/1991 | Japan . |
| 3-13105 | 2/1991 | Japan . |
| 3-37030 | 2/1991 | Japan . |
| 3-221024 | 9/1991 | Japan . |

(List continued on next page.)

*Primary Examiner*—Richard J. Apley
*Assistant Examiner*—Beverly M. Flanagan
*Attorney, Agent, or Firm*—Armstrong, Westerman, Hattori, McLeland & Naughton

[57] ABSTRACT

An endoscope system detachably provided with a cover endoscope possible of being fitted with a cover and used by covering its outer surface with the cover and a coverless endoscope used without being fitted with the cover. A display range and a visual field range of an image that are obtained in the cover endoscope have substantially the same configurations as those of a display range and a visual field range of an image that are obtained in the coverless endoscope.

5 Claims, 29 Drawing Sheets

FOREIGN PATENT DOCUMENTS

| | | |
|---|---|---|
| 3-101903 | 10/1991 | Japan . |
| 3-101904 | 10/1991 | Japan . |
| 3-101905 | 10/1991 | Japan . |
| 3-101906 | 10/1991 | Japan . |
| 3-101907 | 10/1991 | Japan . |
| 3-101901 | 10/1991 | Japan . |
| 3-101902 | 10/1991 | Japan . |
| 4-325138 | 11/1992 | Japan . |

ENDOSCOPE IMAGE

ENDOSCOPE IMAGE

FIG.31(a)
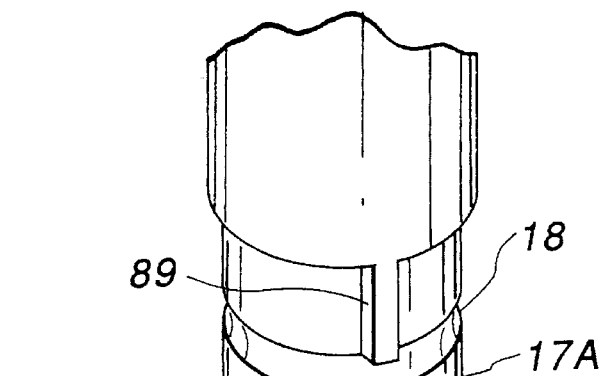
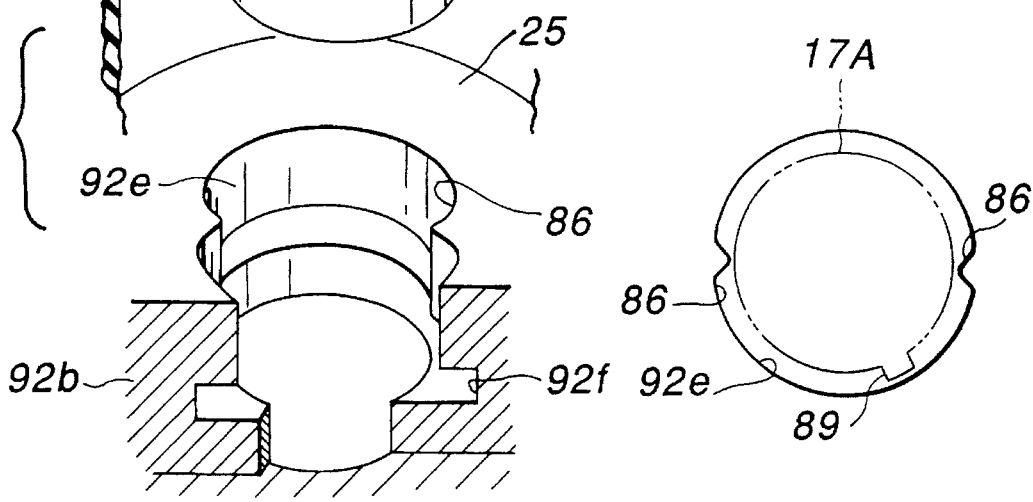
FIG.31(b)
FIG.32
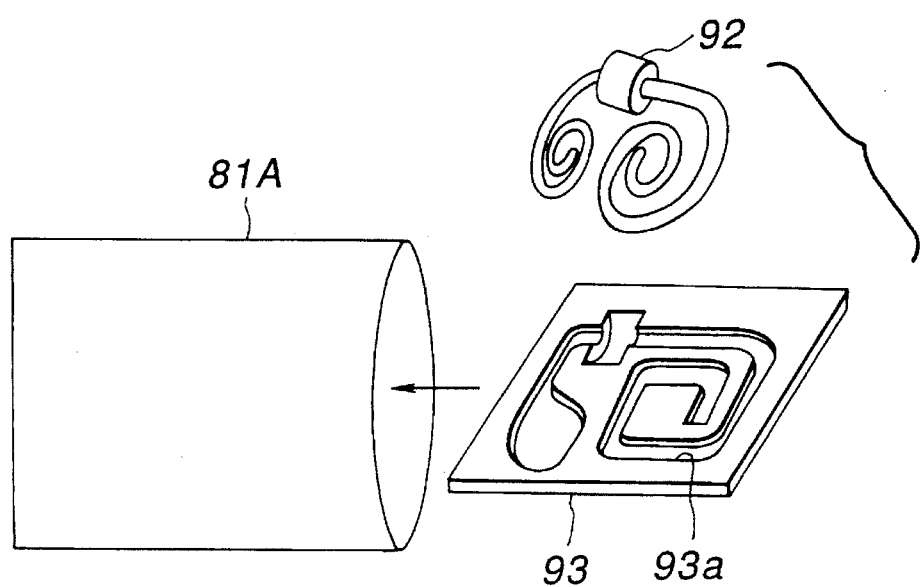

FIG. 42(a)
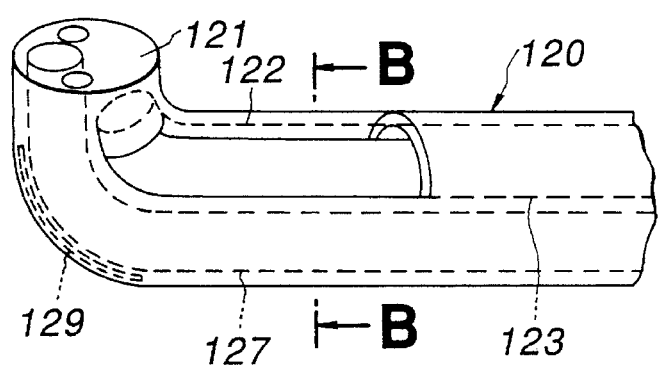
FIG. 42(b)
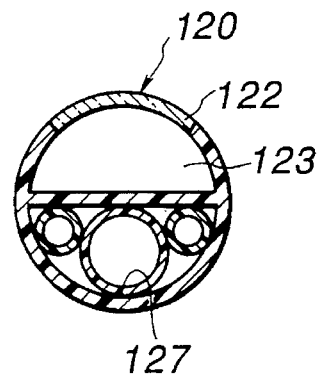
FIG. 43 (a)
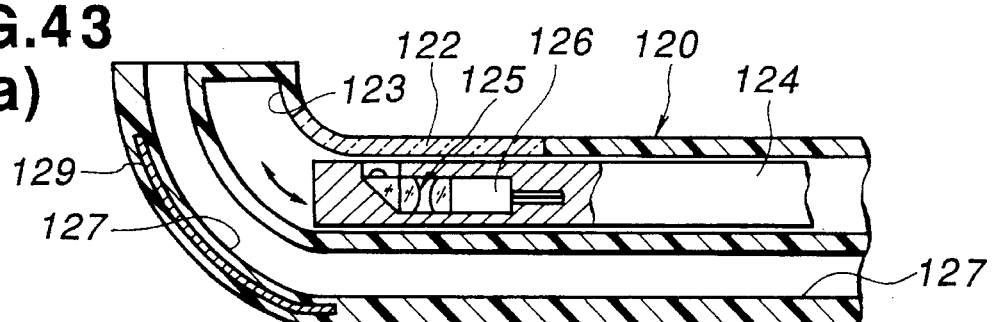
FIG. 43 (b)
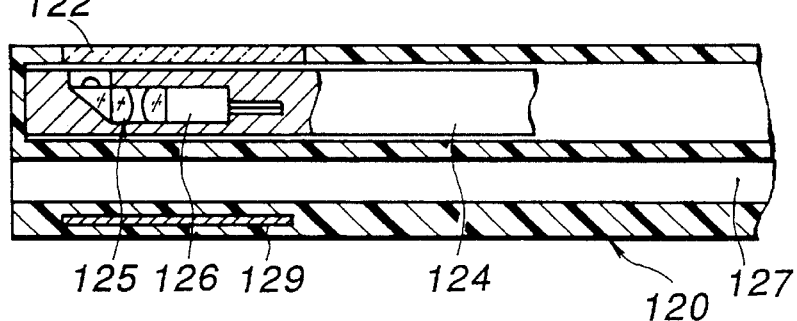
FIG. 44(a)
FIG. 44(b)
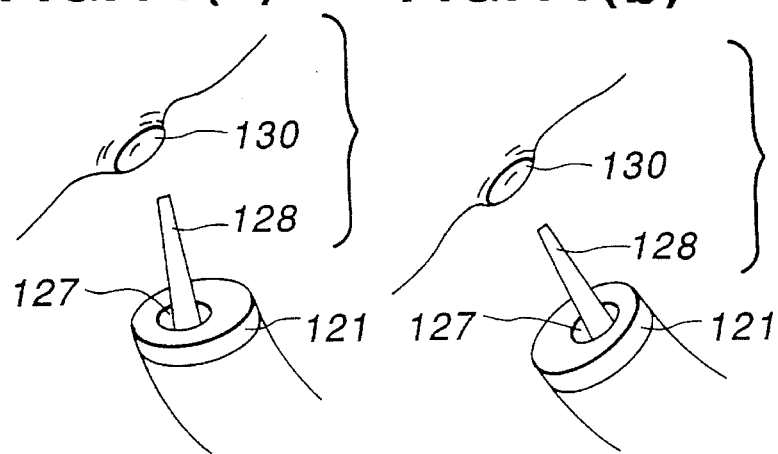

ENDOSCOPE SYSTEM, COVER TYPE ENDOSCOPE UNIT, CHANNELED COVER TYPE ENDOSCOPE UNIT, HOLDING TOOL IN ENDOSCOPE SYSTEM, AND HOUSING MEMBER OF COVER TYPE ENDOSCOPE UNIT

BACKGROUND OF THE INVENTION

1. Field of the Invention

The present invention relates to an endoscope system including a cover endoscope and a coverless endoscope, a cover type endoscope unit covered with an endoscope cover capable of preventing contaminations on the endoscope, a channeled cover type endoscope unit having a channel formed in the endoscope cover, a holding tool in the endoscope system which holds the cover endoscope, etc. and a housing member of the cover type endoscope unit which houses the endoscope cover, etc.

2. Related Art and Prior Art Statement

An endoscopic examination involves the use of a clean endoscope that has been sufficiently washed and disinfected before the examination.

The endoscope is, after being employed in the somatic cavity of the patient, washed and disinfected. The washing and disinfection are, however, very time-consuming. Under such circumstances, there has been in recent years proposed a disposable cover type endoscope unit in place of a conventional repetitive-use endoscope (coverless endoscope) when effecting the endoscopic examination.

The cover type endoscope unit consists of a combination of an endoscope cover fitted to the outer periphery of an endoscope insert part or the like and a cover endoscope inserted into the endoscope cover. The cover type endoscope unit may include those disclosed in, e.g., Japanese Patent Post-Exam Publication No. 2-54734 and U.S. Pat. No. 3,162,190.

Generally in the cover endoscope fitted with the endoscope cover, the insert part incorporates an imaging system or viewing optical system and a light guide fiber.

There is herein a possibility in which a treatment tool channel, an air supply conduit and a water supply conduit are contaminated with body fluids. Those conduits are elongate and therefore hard to clean and disinfect. Accordingly, some of the endoscope covers are equipped with conduits each opened at both ends such as a treatment tool channel, an air supply conduit and a water supply conduit.

The insert part of the cover endoscope is previously washed and disinfected. Then, the endoscope is inserted into the somatic cavity of the patient while the insert part of the endoscope is covered with the endoscope cover. After being employed, the endoscope cover is removed and then abandoned. The endoscope cover is thus disposable for every patient. The endoscope is not therefore required to be washed and disinfected. The operation is very simple. Then, the endoscope is continuously usable without re-washing and re-disinfection.

By the way, the endoscope system using the endoscope cover has a different construction from the presently-employed coverless endoscope (i.e., an endoscope used with no cover). No consideration is therefore given to a relativity between the coverless endoscope and an image viewable therethrough, a configuration of a manipulation part and a manipulability.

The endoscope requires a well-experienced manipulation. If unexperienced in terms of manipulating technique, it may happen that an undesirable strong force is applied to the somatic cavity. The well-experienced manipulating technique is required for preventing the somatic wall from being damaged and the patient from undergoing an excessive pain.

While on the other hand, even a well-skilled operator in terms of manipulating technique has to get accustomed to the manipulating feeling when dealing with an endoscope system which causes a different manipulation feeling and a different visual field. It is therefore required that a careful examination be effected so as not to give the excessive pain to the patient especially for a period during which the operator gets accustomed.

Hence, it is desirable that even the cover endoscope proposed in recent years be used with a similar feeling to that in the conventional coverless endoscope.

Further, in the endoscope system using the endoscope cover, the distal end thereof is required to be covered therewith. Cover lenses have to be provided in positions corresponding to a viewing optical system and illumination optical systems of the cover endoscope.

Accordingly, it follows that a field angle is narrowed corresponding to a thickness of the cover glass. If narrowed, the manipulating feeling becomes different. Besides, a more careful examination is required to be conducted to prevent an oversight of the diseased part due to an increase in dead angle.

As described above, it is desirable that even the endoscope system to which the cover endoscope is connected be employed with a similar feeling to that in the conventional coverless endoscope system.

Then, the subject may suffer from the excessive pain because of a difference in impression that is derived from configurational differences on screen and in range of visual field from those in the conventional system, an unfitted manipulating feeling and a forcible insertion as well. Further, the oversight of the diseased part is induced due to the difference in configuration of a visually accustomed screen. To prevent such things, the manipulator is required of much carefulness.

Still further, the cover endoscopes in the related art are disclosed in U.S. Pat. No. 4,646,722 and U.S. Pat. No. 5,050,585. Each of those cover endoscopes includes a locating member for locating the channel. The cover endoscope and the insert part cover section are fixed to each other.

The cover endoscope has such an inevitability in terms of structure that a forceps outlet is opened upwardly (in an UP-direction) of the visual field or in a position in accordance with its layout.

On the other hand, the coverless endoscope is typically constructed so that the forceps insert inlet is protruded from the left downward side with respect to the UP-direction defined as a bending direction in the case of, e.g., an upper digestive duct oriented endoscope but from the right downward side in the case of a lower digestive duct oriented endoscope.

The well-experienced examiner to the manipulation thereof takes the trouble to bring the forceps outlet to a safety position by letting the protruding direction of the treatment tool apart from the somatic wall when employing the treatment tool in a location close to the somatic wall. The examiner then protrudes the treatment tool. The reason for this lies in a difficulty to make the treatment tool reach a target location if the forceps outlet is positioned close to the somatic wall.

The situation is the same with the cover endoscope disclosed in the Patent Publications given above. A position of the opening (outlet) is regulated in terms of structure. The treatment tool is positioned too close to the somatic wall, with the result that the bending manipulation is not performed well. This also results in worsening of an aiming performance of the treatment tool. For this reason, the user may feel a difficulty in use.

Further, the positional relation between the outlet of the treatment tool and the viewing window is fixed in the conventional cover endoscope. The user therefore feels the difficulty in use because of the treatment coming out from an unaccustomed position (from the direction of visual field) depending on an object to be viewed.

The manipulation part of the endoscope is Grasped with the left hand. It is a common practice that the insert part is fed with the right hand when inserting the insert part; and the treatment tool is also inserted from the forceps insert port with the right hand. In the coverless endoscope that has hitherto been employed, an opening of the forceps insert port is formed on the right side in the UP-direction (upwards in the bending direction) in the manipulation part, thereby facilitating the manipulation of the treatment tool with the right hand.

In the case of the cover endoscope, however, the position of the forceps insert port is not prescribed in unification. In some cases, the insert port is opened in a DOWN-direction (downwards) in the manipulation part. Based on such a construction, the insertability of the treatment tool gets worse so much. Further, even in the endoscope having the forceps insert port formed in the insert part cover section covered on the endoscope insert part, if provided on the left side in the DOWN-direction in the manipulation part, the insertability similarly declines.

Then, if the insertability is poor, the user makes an attempt to direct the forceps insert port in an easy-to-insert direction with a twist of the left hand. It follows that even a distal end portion is simultaneously twisted. When the distal end portion is shifted, the visual field also shifts, with the result that the diseased part fails to be found out, or the aiming performance declines.

In addition, the operator accustomed to the use of the coverless endoscope has hitherto tended to feel the difficulty in use of the cover endoscope to such an extent that the operator does not concentrate on the examination.

Further, when utilizing the cover endoscope in combination with the coverless endoscope, and if the manipulability differs, the endoscopic examination can not, it seems, be smoothly conducted.

The consideration has to be given to the following points other than the above-mentioned in the cover type endoscope system. When the fitting the endoscope cover, the cover endoscope is likely to be contaminated; or alternatively, when removed, there is a likelihood in which the contaminants adhered to the endoscope cover are diffused to the surroundings. It is thus impossible to keep the ambient environment in a sanitary state. The manipulator is also required of the cautious manipulation to avoid such a situation.

Further, the endoscope cover consists of a plurality of cover members for covering on the whole cover endoscope when examined. The endoscope cover has to be supplied together with a mouthpiece, etc. in a well-sanitized state. Then, the endoscope cover is constructed of the plurality of cover members, and hence, if those cover members are not completely prepared, a trouble is caused in the examination.

Especially when even one of the cover members of the endoscope cover lacks, there exists a possibility of the cover endoscope being contaminated during the examination. It follows that the examination can not be started.

OBJECTS AND SUMMARY OF THE INVENTION

It is a primary object of the present invention to provide a cover type endoscope unit in which a range of visual field is not narrowed by an endoscope cover when fitted with the endoscope cover.

It is another object of the present invention to provide a cover type endoscope unit capable of exhibiting an excellent manipulability in which manipulating and viewing can be performed without unfitted feeling as in the coverless endoscope.

It is still another object of the present invention to provide an endoscope system capable of exhibiting the excellent manipulability in which manipulating and viewing can be effected without the unfitted feeling as in the coverless endoscope in such an endoscope system that the coverless endoscope and a cover endoscope are detachably connectable thereto.

It is a further object of the present invention to provide a channeled cover type endoscope unit capable of permitting a treatment tool to protrude from a well-accustomed direction of visual field and improving an aiming performance as compared with the coverless endoscope.

It is a still further object of the present invention to provide a channeled cover type endoscope unit capable of exhibiting an excellent insertability of the treatment tool and an excellent manipulability of the endoscope.

It is a yet further object of the present invention to provide an endoscope system capable of employing the treatment tool with the same feeling as that in the coverless endoscope and inducing no decline in the aiming performance.

It is an additional object of the present invention to provide to provide a holding tool in an endoscope system in which a cover endoscope is not contaminated when fitting and removing an endoscope cover.

It is a still additional object of the present invention to provide a holding tool in an endoscope system in which contaminants are not diffused to the surroundings when removing the endoscope cover.

It is a yet additional object of the present invention to provide a housing member of a cover type endoscope unit capable of preventing lacks of a plurality of cover members constituting the endoscope cover and necessary parts as well and of effecting an endoscopic examination while a cover endoscope is completely covered therewith.

To accomplish the forgoing objects, according to one aspect of this invention, there is provided an endoscope system comprising a cover endoscope covered with an endoscope cover and a coverless endoscope fitted with no endoscope cover, these cover and coverless endoscopes being detachably provided therein. At least one of a screen and a range of visual field obtained in the cover endoscope has the same configuration as that of at least one of a screen and a range of visual field obtained in the coverless endoscope.

According to another aspect of this invention, there is provided a channeled cover type endoscope unit comprising a channeled endoscope cover and a channeled cover endoscope. The channeled endoscope cover is covered on at least an insert part of the channeled cover endoscope. The channeled endoscope cover includes an insert part cover section formed at the distal end of an opening outlet of a treatment tool channel from which a treatment tool protrudes. The insert part cover section and the channeled endoscope cover are rotatably constructed in a state where the channeled cover endoscope is installed in the endoscope insert channel of the insert part cover section.

Other characteristics and advantages of the present invention will sufficiently become apparent during the following full discussion.

BRIEF DESCRIPTION OF THE DRAWINGS

FIG. 1 is a view illustrating an external appearance of a whole endoscope system to which a cover endoscope is connected;

FIG. 2 is a view showing a construction of the endoscope system to which a coverless endoscope is connected;

FIG. 3 is a view illustrating the cover endoscope;

FIG. 4 is a view showing external appearances of the cover endoscope and the coverless endoscope;

FIG. 5 is a side sectional view illustrating a distal end in a cover type endoscope unit;

FIG. 6 is a perspective view illustrating the distal end of the cover endoscope;

FIG. 7 is a perspective view illustrating a distal end of an insert part cover section;

FIG. 8 is a view showing a construction of a manipulation part cover section;

FIG. 9 is a view illustrating a construction of a universal cord cover section;

FIG. 10 is an explanatory view showing how a field angle of the endoscope is intercepted;

FIG. 11 is an explanatory view showing a range of visual field and an optical system in the cover type endoscope unit;

FIG. 12 is an explanatory view illustrating configurations of an objective optical system of the endoscope and a monitor display;

FIG. 13 is a block diagram showing signal processing in the cover endoscope in a simultaneous imaging system;

FIG. 14 is a block diagram showing signal processing in the coverless endoscope in the simultaneous imaging system;

FIG. 15 is a block diagram showing signal processing in the cover endoscope in a field-sequential imaging system;

FIG. 16 is a block diagram showing signal processing in the coverless endoscope in the field-sequential imaging system;

FIG. 17 is an explanatory view how cover sections are housed;

FIG. 18 is an explanatory view showing how the cover sections are housed;

FIG. 19 is an explanatory view showing how the cover sections are housed;

FIG. 20 is a view illustrating an external appearance showing the whole endoscope system to which the cover endoscope is connected;

FIG. 21 is a view illustrating the cover endoscope;

FIG. 22 is a view illustrating a construction of a manipulation part cover section;

FIG. 23 is an explanatory view showing a viewing mask;

FIG. 24 is a view showing an external appearance of the whole endoscope system to which the cover endoscope is connected;

FIG. 25 is a side sectional view illustrating the distal end in the cover type endoscope unit;

FIG. 26 is a perspective view showing the distal end of the cover endoscope;

FIG. 27 is a perspective view illustrating a distal end of the cover;

FIG. 28 is a view illustrating an external appearance of the cover endoscope;

FIG. 29 is an explanatory view showing how the insert part cover section rotates about the endoscope;

FIG. 30 is an explanatory view showing how the treatment tool aims at a target;

FIG. 31 is a view illustrating a construction of a modified example of the third embodiment;

FIG. 32 is an explanatory view showing package;

FIG. 33 is a view illustrating the whole endoscope system to which the cover endoscope is connected;

FIG. 34 is a side sectional view showing the distal end in the cover type endoscope unit;

FIG. 35 is a perspective view illustrating the distal end of the cover endoscope;

FIG. 36 is a perspective view illustrating the distal end of the insert part cover section;

FIG. 37 is a view showing an external appearance and a construction of the endoscope system to which the coverless endoscope is connected;

FIG. 38 is a view showing an external appearance of the cover endoscope;

FIG. 39 is an explanatory view showing a mounting position of a treatment tool insert port;

FIG. 40 is a perspective view illustrating a cover holding tool in another construction;

FIGS. 41 through 44 show a fifth embodiment of this invention;

FIG. 42 is a view illustrating a construction of the distal end of the insert part cover section;

FIG. 43 is an explanatory view showing an operation of the cover type endoscope unit; and FIG. 44 is an explanatory view showing how to aim at the target in the cover type endoscope unit.

DETAILED DESCRIPTION OF THE PREFERRED EMBODIMENTS

Embodiments of the present invention will hereafter be discussed with reference to the drawings.

Figure 1:
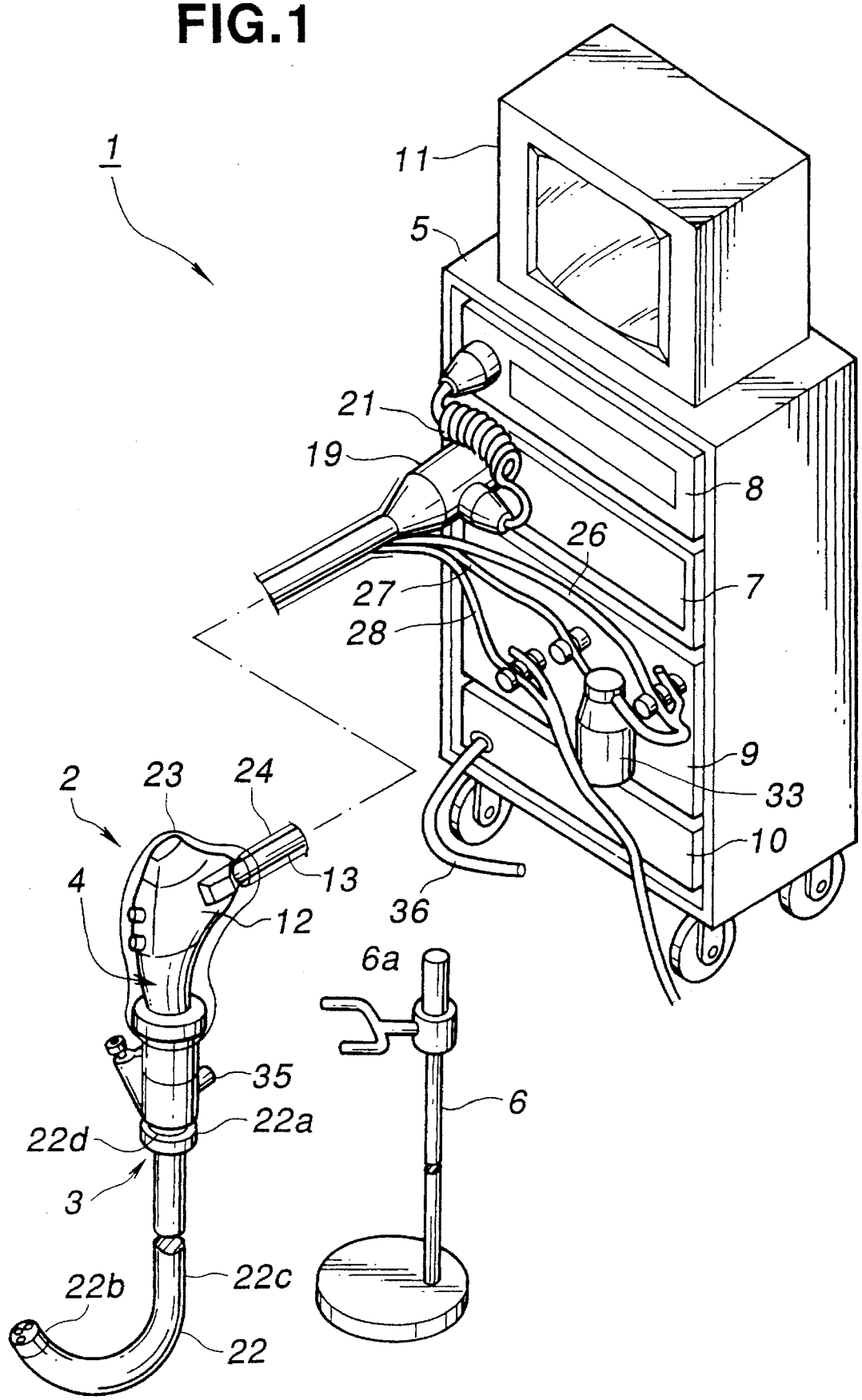
FIGS. 1 through 19 show a first embodiment.

An endoscope system 1 illustrated in FIG. 1 is an apparatus to which a channeled endoscope cover fitted type endoscope unit (hereafter simply referred to as a cover type endoscope unit) 2 and an endoscope unit with no channel which will be mentioned later are detachably connected.

The cover type endoscope unit 2 comprises a combination of a channeled endoscope cover (hereafter simply called a cover) 3 and a channeled endoscope cover endoscope (hereafter simply called a cover endoscope) 4. The cover type endoscope unit 2 is classified as an electronic type.

Further, the cover 3 is covered on an insert part of the cover endoscope 4, thus eliminating the necessity for cleaning and disinfection of the endoscope after an examination has been done.

The endoscope system 1 includes the cover type endoscope unit 2, a cart 5 incorporating a variety of peripheral devices connected to this cover type endoscope unit 2 and a cover holding tool 6 for holding the cover type endoscope unit 2.

The cart 5 accommodating the peripheral devices shown in FIG. 1 houses, e.g., a light source unit 7, a video processor 8, a fluid control unit 9 and a channeled endoscope cover dilator (hereafter simply called a dilator) 10. Besides, a monitor 11 is mounted on the top plate of the cart 5.

The light source unit 7 emits illumination light towards the cover endoscope 4 of the cover type endoscope unit 2. Further, the video processor 8 connected to the electronic type cover endoscope 4 converts an electric signal transmitted from the same endoscope 4 into a standard video signal. The video processor 8 outputs the video signal to the monitor 11. The monitor 11 displays, on receiving the video signal, an endoscope image thereon.

Further, the fluid control unit 9 supplies the air and water via conduits provided inwardly of the cover 3, which will be stated later. For this purpose, the fluid control unit 9 is equipped with a water supply source and an unillustrated air supply source. The conduits connected to the air and water supply sources are so controlled as to be opened and closed by means of solenoid valves.

Additionally, the dilator 10 works to feed the air into the cover 3 to dilate this cover 3. The dilation thereof facilitates an installation or a removal of the cover endoscope 4 into or from the cover 3.

Figure 3:
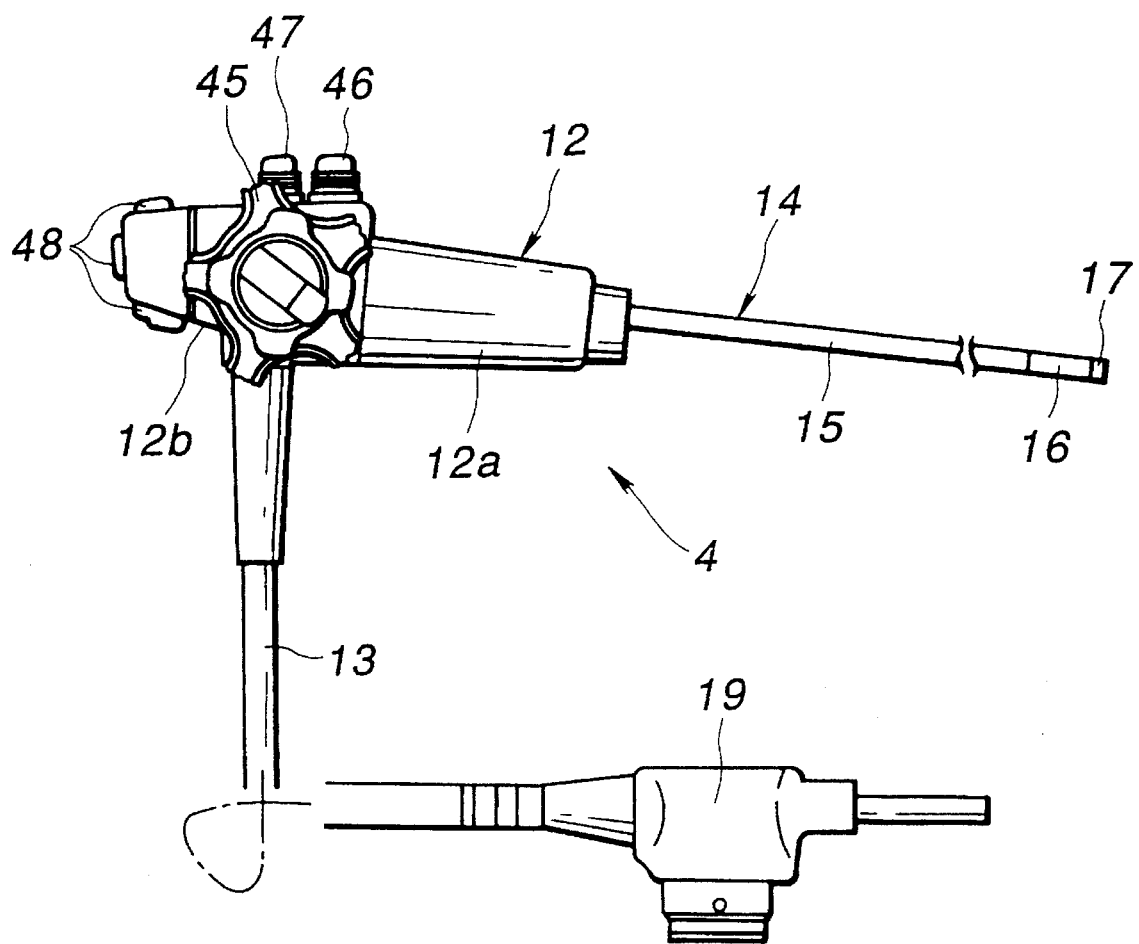

The cover endoscope 4 is constructed, as depicted in FIG. 3, of a manipulation part 12, a universal cord 13 extending from a side portion of this manipulation part 12 and an insert part 14 connected to this manipulation part 12. As shown in FIG. 3, the insert part 14 of the cover endoscope 4 is constructed of, sequentially from a proximal end of the manipulation part 12 toward its distal end, a flexible tube portion 15, a bendable portion 16 and a hard distal end portion 17.

Figure 6:
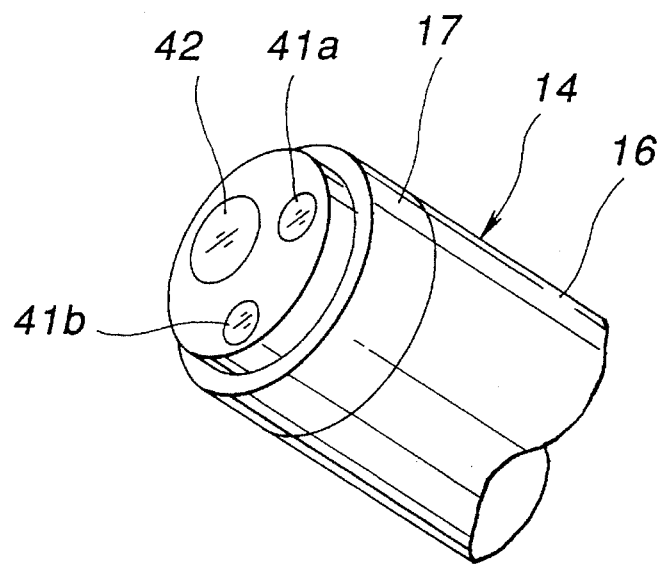

The insert part 14 of the cover endoscope 4 having a small diameter is formed in a cylindrical shape in section. Further, the distal end portion 17 of the cover endoscope 4 is, as depicted in FIG. 6, provided with illumination optical systems 41a, 41b and an objective optical system 42. Note that the insert part 14 of the endoscope 4 may assume a D-shape in section.

An outgoing end of an unillustrated light guide fiber is provided at the rear end of the illumination optical systems 41a, 41b. This light guide fiber is inserted through the insert part 14, the manipulation part 12 and the universal cord 13.

A connector 19 is provided at the end of the universal cord 13. This connector 19 is detachably connected to the light source unit 7. Then, the illumination light emitted from the light source unit 7 is led to an incident end of the light guide fiber.

Figure 5:
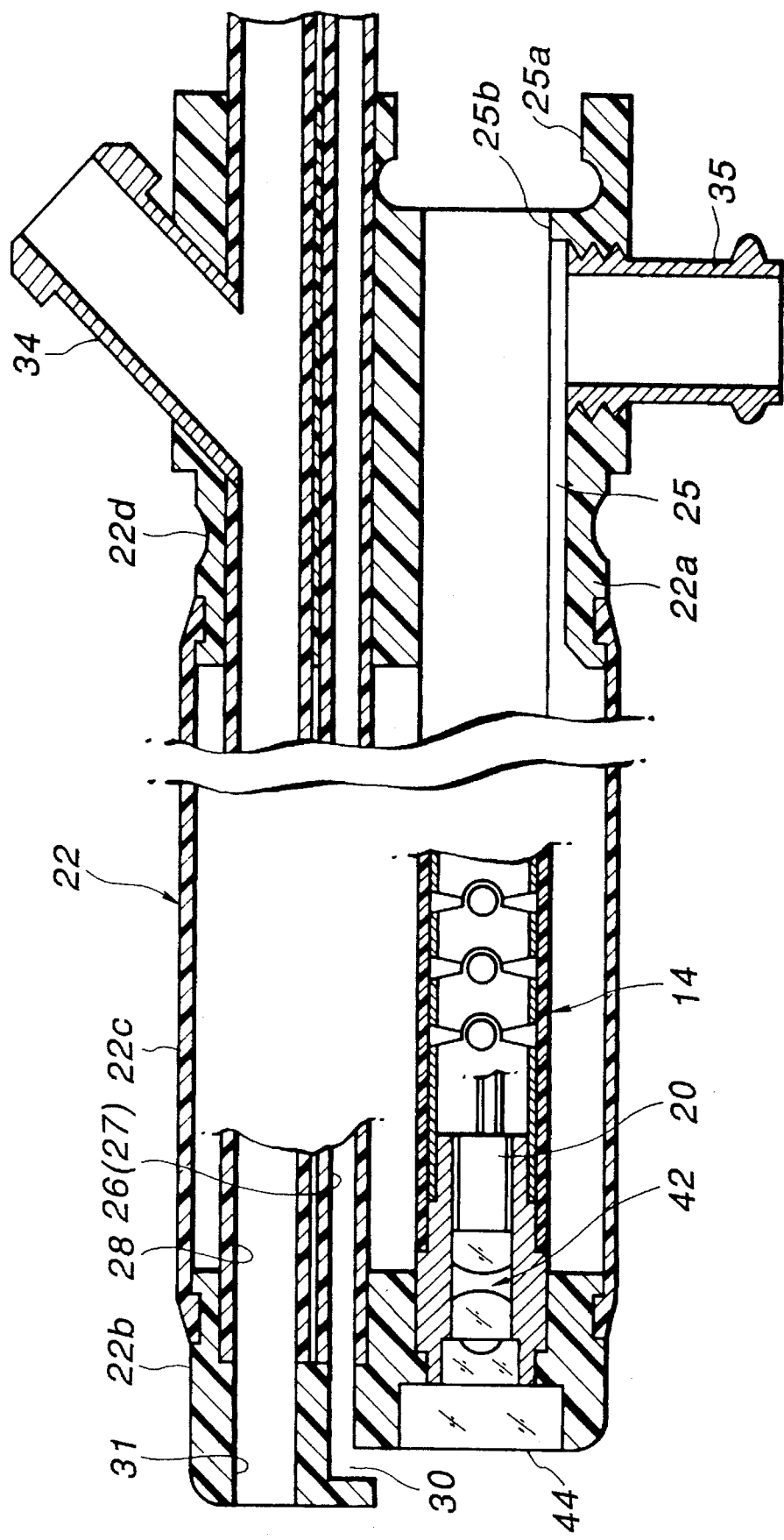

As illustrated in FIG. 5, a solid-state image sensor 20 for converting an incoming optical image into an electric signal is disposed at a rear end of the objective optical system 42. The electric signal outputted from this solid-state image sensor 20 is inputted to the video processor 8 via a signal cord 21 extending from a side portion of the connector 19 shown in FIG. 1.

As depicted in FIG. 3, the proximal end of the manipulation part 12 serves as a grasping portion 12a. A manipulation part body 12b connected to the upper side of the grasping portion 12a is provided with an angle knob 45, an air/water supply control switch 46, a suction control switch 47, a function switch 48 for photographing, etc.

The angle knob 45 is detachably attached to the manipulation part body 12b. The manipulation part 12 is constructed to acquire the same manipulating feeling as that in a coverless endoscope which will be mentioned later.

As illustrated in FIG. 1, the cover 3 with which the cover endoscope 4 is covered comprises an insert part cover section 22, a manipulation part cover section 23 and a universal cord cover section 24. The insert part cover section 22 of the cover 3 is covered on the insert part 14 of the cover endoscope 4. Further, the manipulation part cover section 23 of the cover 3 is covered on the manipulation part 12 of the cover endoscope 4 as well as on three lines of conduits that will be stated later. Besides, the universal cord cover section 24 of the cover 3 is covered on the universal cord 13 of the cover endoscope 4 as well as on three lines of conduits that will be mentioned later. Then, the cover endoscope 4 entirely fitted with the cover 3 is employed for an examination while being watertightly covered therewith.

Note that the cover holding tool 6 shown in FIG. 1 is constructed to take hold of, when installing the insert part cover section 22 on the cover endoscope 4, a hold groove cut in the insert part cover section 22 that will be stated later with the aid of an arm 6a thereof. The endoscope 4 can be thereby held without touching on the cover 3 with a hand. The operation is therefore sanitary and thus facilitated.

FIG. 5 is a side sectional view showing a state where the insert part cover section 22 of the cover 3 is covered on the cover endoscope 4.

The insert part cover section 22 is intended to isolate the insert part 14 of the cover endoscope 4 from the external environment. This insert part cover section 22 is formed in an elongate shape. An endoscope manipulation part fixing mouth portion (simply called a mouth portion) 22a on the near-at-hand side and a distal end portion 22b are each formed of a hard material, e.g., a resin. Further, a mid-part between the mouth portion 22a of the insert part cover section 22 and the distal end portion 22b thereof is covered with an insert part cover sheath 22c composed of a flexible material. The insert part cover sheath 22c is formed to have a wall thickness on the order of 0.1 mm~1 mm.

Moreover, the insert part cover section 22 is internally formed with an endoscope insert channel 25 enough to insert the insert part 14, an air supply tube 26, a water supply tube 27 and a suction tube 28.

On the side of the proximal end of the endoscope insert channel 25, an opening 25a for inserting the insert part 14 is formed in the mouth portion 22a. Further, an airtight fitting portion 25b is formed inwardly of the opening 25a of the endoscope insert channel 25. The proximal end of the endoscope manipulation part 12 is fitted in the opening 25a of the endoscope insert channel 25. Besides, the airtight fitting portion 25b is formed to have a diameter enough to be tightly fitted to the endoscope insert part 14. Further, the endoscope insert channel 25 is closed at the distal end portion 22b. The insert part 14 of the cover endoscope 4 is isolated airtightly from the external environment.

Figure 7:
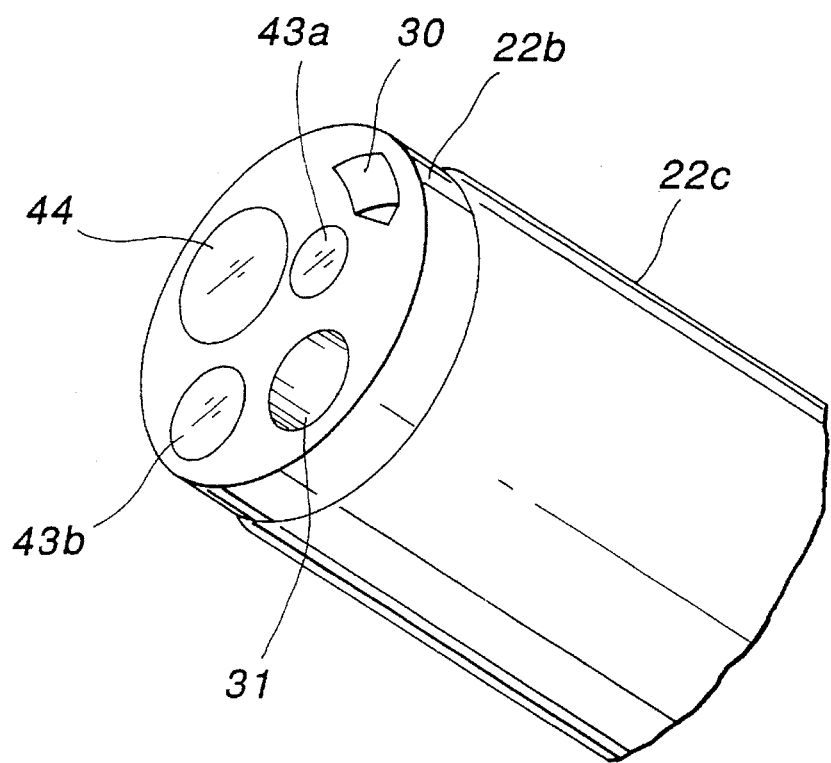

The distal end portion 22b of the insert part cover section 22 is, as illustrated in FIG. 7, formed with transparent windows 43a, 43b, 44 at the distal end of the endoscope insert channel 25. These windows 43a, 43b, 44 are each disposed in face-to-face relationship to the illumination optical systems 41a, 41b and the objective optical system 42 of the cover endoscope 4.

Further, the distal end portion 22b of the insert part cover section 22 is formed with an air (or water) supply nozzle 30 opened toward the window 44 and an opening 31 as well. The air (or water) supply nozzle 30 connectively communicates with the air supply tube 26 (or water supply tube 27). The opening 31 also connectively communicates with the suction tube 28.

Additionally, the air supply tube 26, the water supply tube 27 and the suction tube 28 extend from the mouth portion 22a further towards the near-at-hand side. The ends portions thereof are each opened. As depicted in FIG. 1, the air supply tube 26 connectively communicates with an unillustrated air supply source of the fluid control unit 9. Further, the water supply tube 27 connectively communicates with the air supply source via a water supply tank 33 serving as a water supply source. Still further, the suction tube 28 connectively communicates with an unillustrated suction source as well as with an unillustrated suction bottle.

As shown in FIG. 5, a treatment tool insert port 34 and a dilation tube mouth 35 are formed protrusively from the sides of the mouth portion 22a. The dilation tube mouth 35 has its internal conduit communicating with the endoscope insert channel 25. A dilation tube 36 connected to the dilator 10 is detachably connected to the dilation tube mouth 35.

The treatment tool insert port 34 protrudes backwards in the axial direction of the insert part cover section 22. An internal conduit of the treatment tool insert port 34 is opened at its protruded end and communicates with the suction conduit 28 at the other end thereof. That is, the suction conduit 28 serves as a conduit of the treatment tool channel on the side of its distal end.

Cut also in the side outer periphery of the mouth portion 22a is a hold groove 22d engaging with the arm 6a of the cover holding tool 6 when holding the insert cover section 22.

Figure 2:
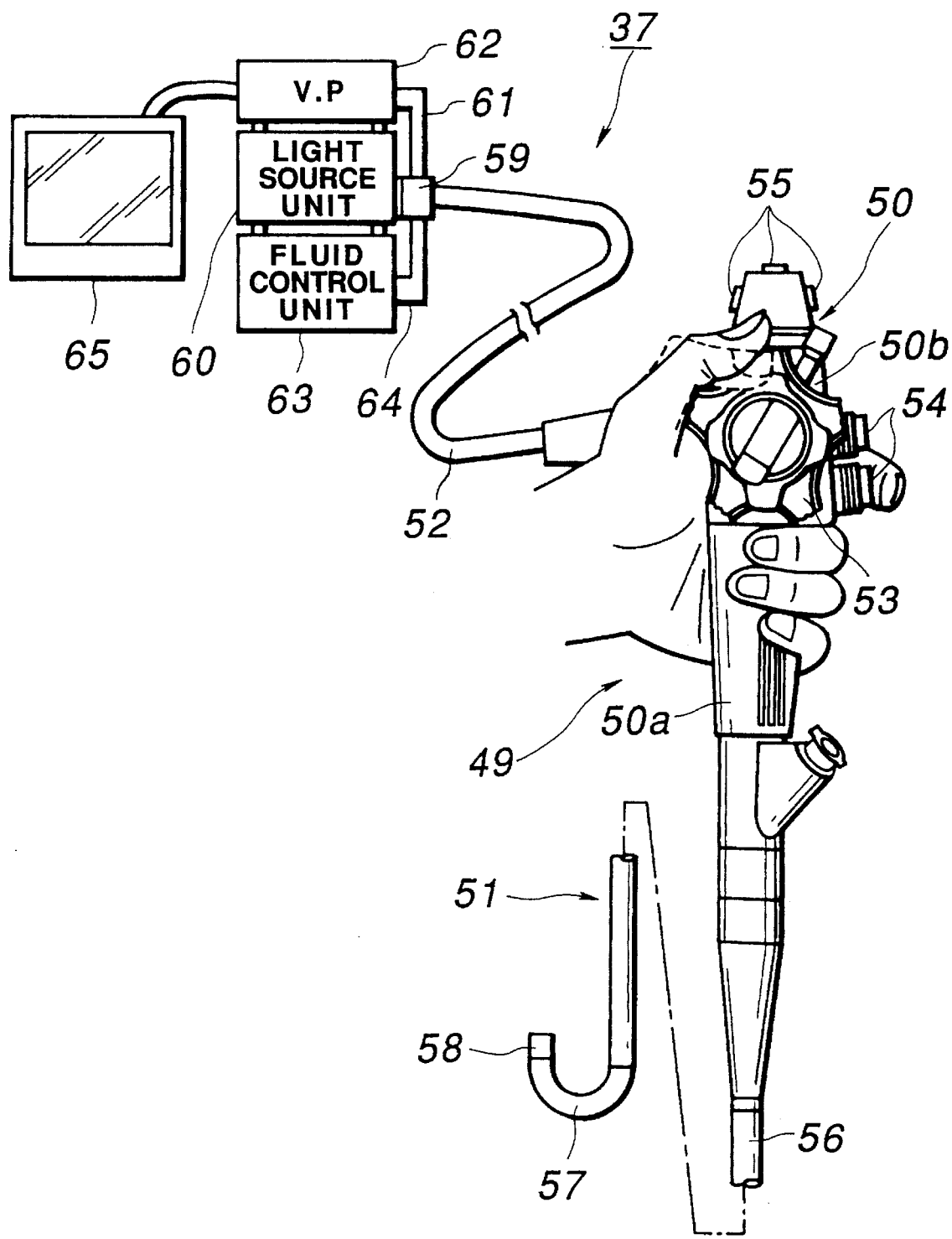

On the other hand, a configuration of the endoscope system of the coverless endoscope is shown as below by way of one example. FIG. 2 shows a configuration of an endoscope system 37 in a state where the coverless endoscope is connected.

The coverless endoscope 4 shown in FIG. 2 includes a manipulation part 50, an insert part 51 and a universal cord 52. The manipulation part 50 is provided with a grasping portion 50a. A manipulation part body 50b connected to the upper side of the grasping portion 50a is provided with an angle knob 53, an air/water supply/suction control switch 54 and a function switch 55 for photographing, etc.

The insert part 51 is connected to the proximal end of the manipulation part 50. The universal cord 52 extends from the side portion of the manipulation part 50. The insert part 51 is constructed of, sequentially from the proximal end of the manipulation part 50 towards its distal end, a flexible tube portion 56, a bendable portion 57 and a distal end portion 58.

Further, a connector 59 is provided at the end of the universal cord 52. This connector 59 is detachably connected to the light source unit 60. The connector is at the same time connected to a video processor (VP) 62 via a cable 61 extending from the side portion thereof. Connected further to the connector 59 is a connecting tube 64 through which an unillustrated tube within the coverless endoscope 49 communicates with a fluid control unit 63.

A monitor 65 is electrically connected to the video processor 63. The monitor 65 is constructed to display an image formed by an image sensor 66, shown in FIG. 12, in the interior of the endoscope distal end portion 58. Note that an objective optical system 67 is disposed at the distal end of the image sensor 66.

Given next is an explanation of configurations of the manipulation part 12 of the cover endoscope 4 and the manipulation part 50 of the coverless endoscope 49.

The manipulation part 12 of the cover endoscope 4 is formed in much the same configuration as that of the manipulation part 50 of the coverless endoscope 49. The following is one example which will be described with reference to FIGS. 2 through 4. The grasping portion 12a of the cover endoscope 4 is formed so that a size and a shape thereof are, when covered with the manipulation part cover section 23, substantially identical with those of the grasping portion 50a of the coverless endoscope 49.

Figure 4A:
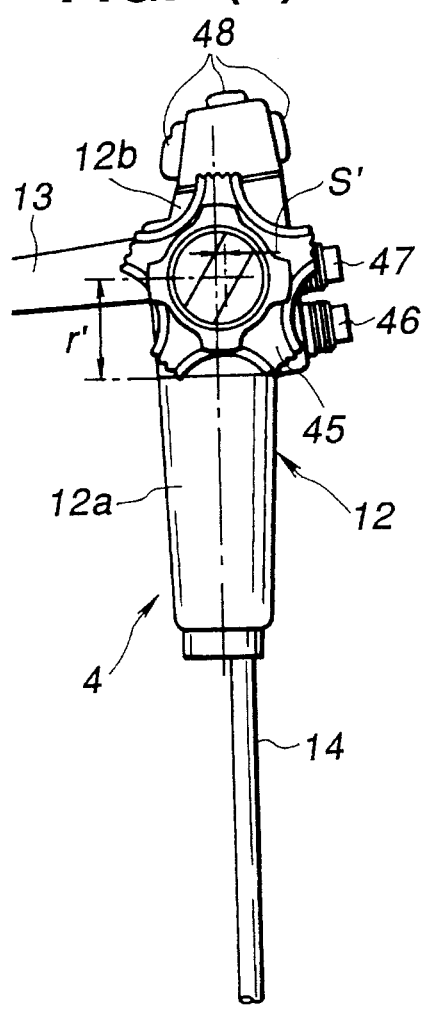
Figure 4C:
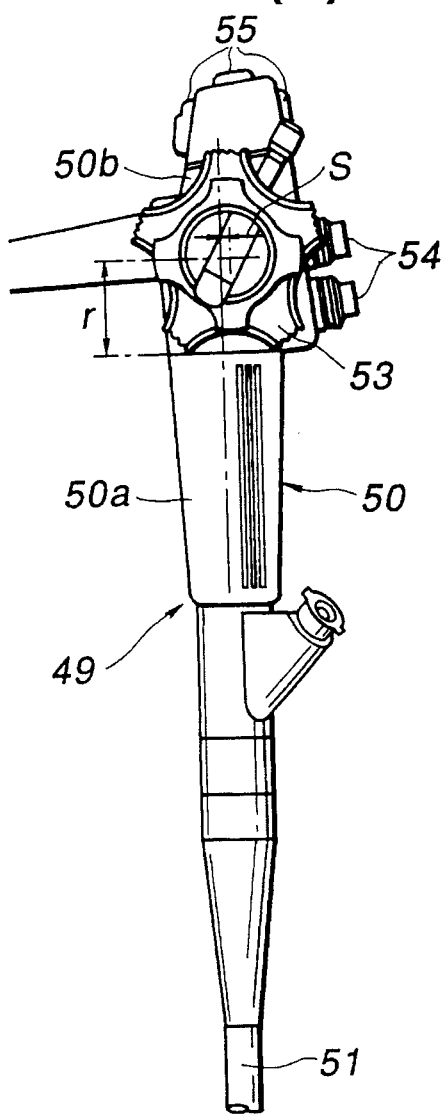
Figure 4B:
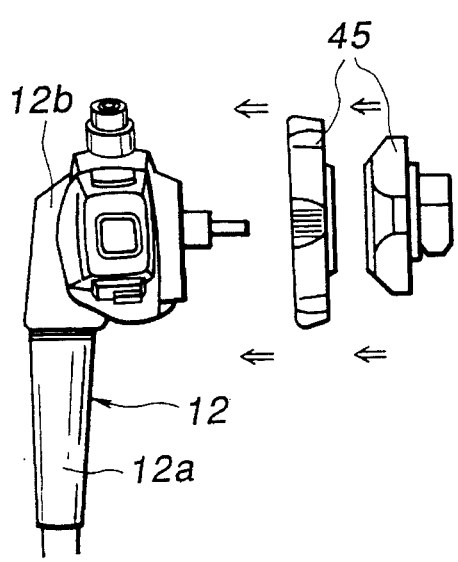
Figure 4D:
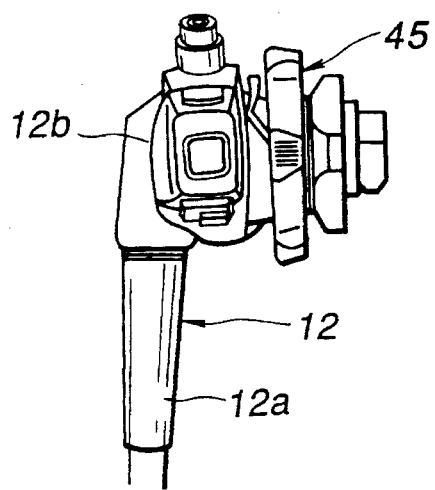

Further, the angle knob 45 has a size and a shape that are substantially identical with those of the angle knob 53 of the coverless endoscope 49. The following is a detailed explanation of an attaching position of the angle knob 45. A shift quantity $s$ of the angle knob 45 from the central axis of the grasping portion 12a shown in FIG. 4(a) is set to 0 mm~20 mm. An installation of the manipulation part body 1 is set as below. The manipulation part body 12b is installed at a distance $r$ on the order of 20 mm~40 mm apart from the boundary with the grasping portion 12a. Namely, as shown in FIG. 4(c), the angle knob 45 is attached substantially in the same way with the angle knob 53 of the coverless endoscope 49.

Based on the construction described above, the manipulation part 12 of the cover endoscope 4 obtains the same manipulation feeling as that in the coverless endoscope.

Figure 8:
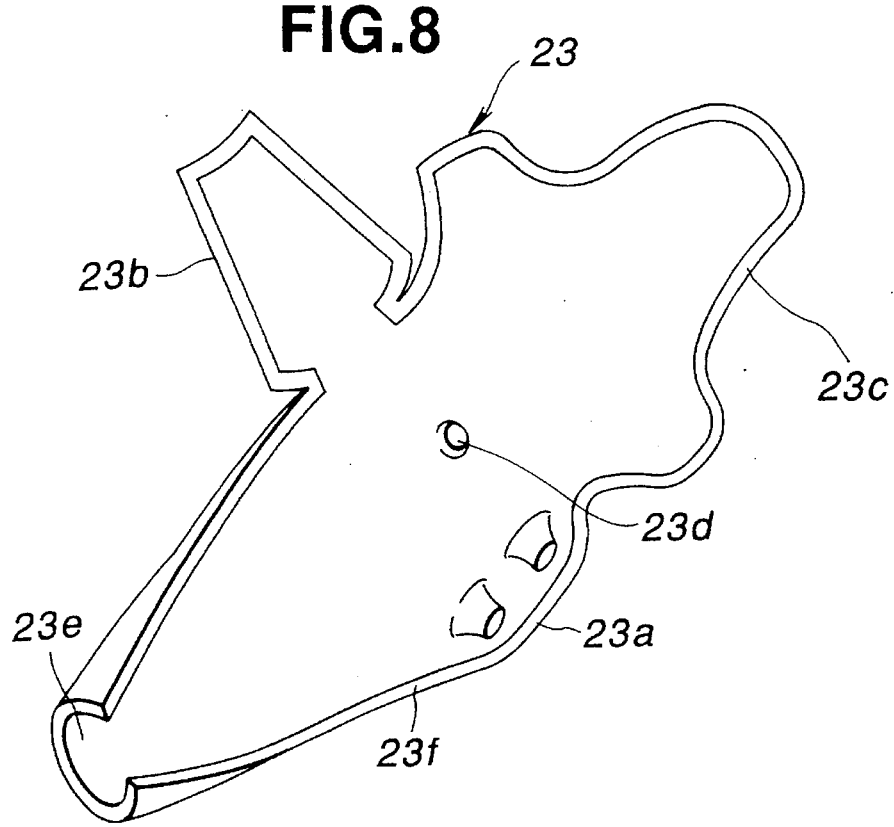

Next, the manipulation part cover section 23 and the universal cord cover section 24 of the cover 3 are constructed in the following manner. The manipulation part cover section 23 shown in FIG. 8 is formed of a soft resin in a sheet-like configuration that is approximately 0.1 mm~2 mm in wall thickness.

The manipulation part cover section 23 consists of a cover main member 23a to be covered on the manipulation part 12, a cord connecting portion cover segment 23b to be covered on the connecting end of the universal cord 13 and a switch portion cover segment 23c to be covered on a head portion of the manipulation part which includes the switch 48, etc.

The cover main member 23a is formed with an angle shaft insert hole 23d to which the angle knob 45 is connected at the center thereof. Further, the cover section 23 has a connecting end 23e at the end of the mouth portion 22a of the insert part cover section.

A fringe of the manipulation part cover section 23 is provided with an adhesive portion 23f for facilitating an installing workability.

Figure 9:
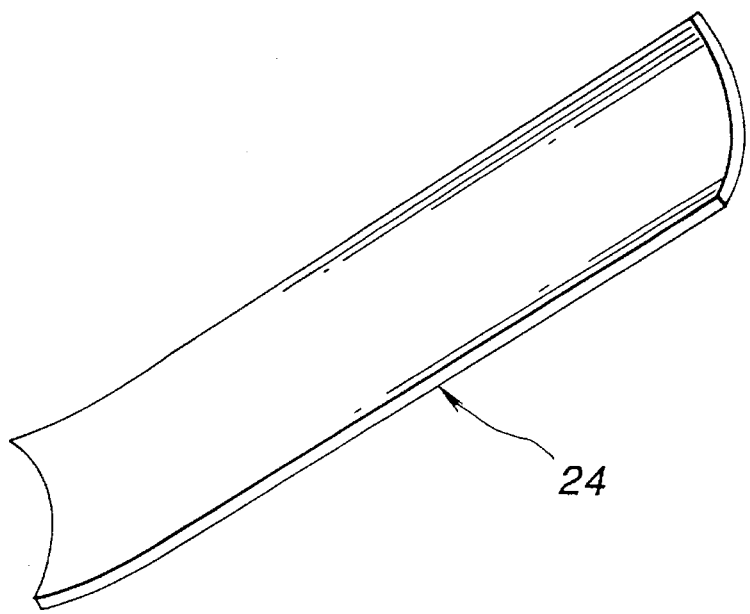

The universal cord cover section 24 shown in FIG. 9 is composed of a soft resin in an elongate sheet-like configuration to have a wall thickness of approximately 0.1 mm~2 mm. A length of the same cover section 24 is set slightly larger than that of the universal cord 13 so as not to form an exposed portion.

Next, the optical system of the cover type endoscope apparatus will be explained with reference to FIGS. 10 through 12.

Figure 10:
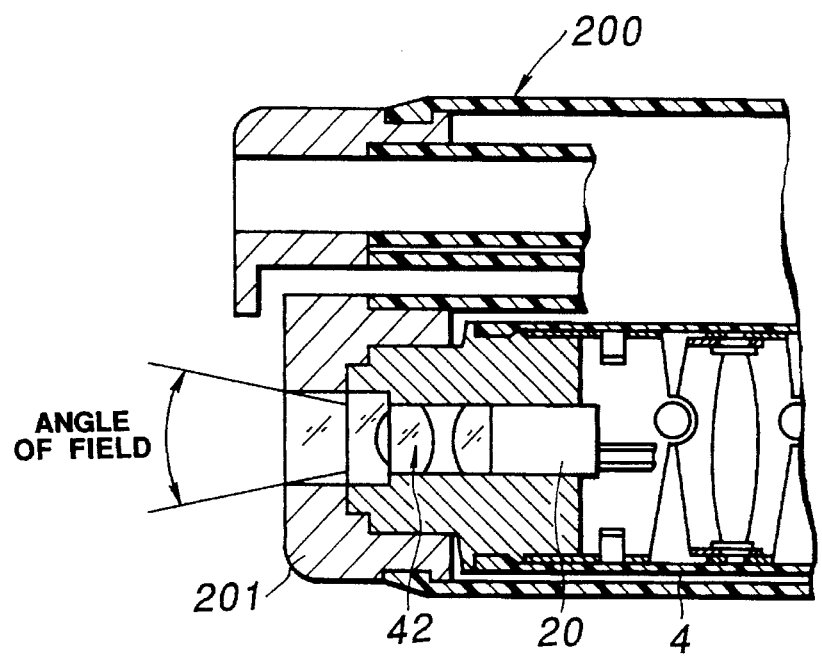
Figure 11A:
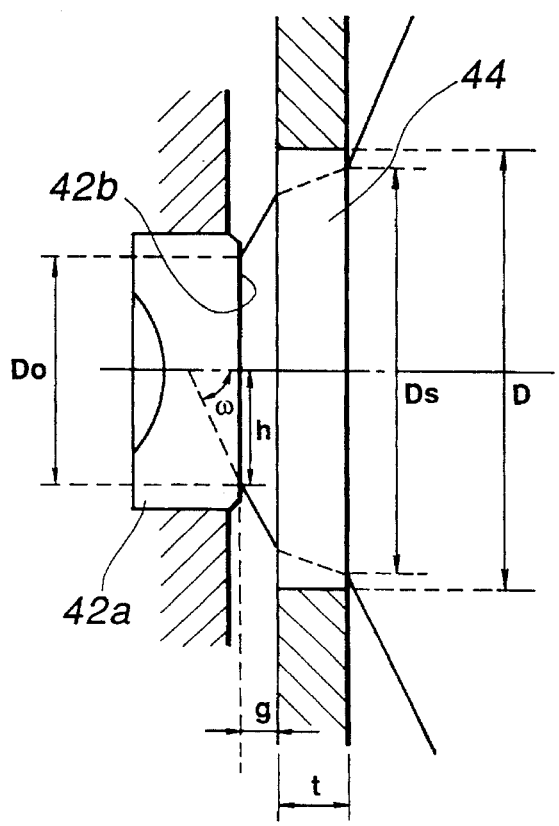
Figure 11B:
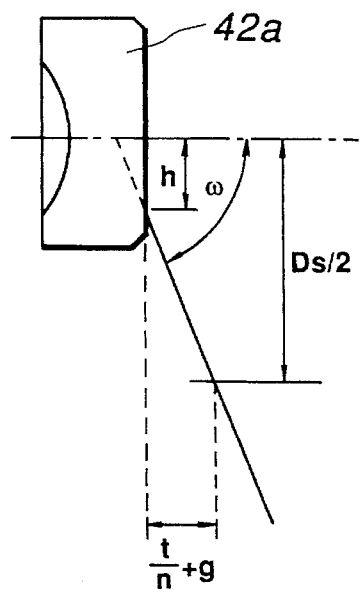

Generally in the case of the endoscope using the cover, as shown in FIG. 10, a visual field is intercepted by a wall thickness of the distal end of a cover 200, thereby narrowing an angle of field. Accordingly, this embodiment provides such a construction that the operator is allowed to use the endoscope without being aware of the cover endoscope with the same visual field as that of the conventionally well-accustomed coverless endoscope. The window 44 of the insert part cover section 22 is formed larger than a major diameter of the objective optical system 42 of the endoscope. A view angle Q1 to be obtained as shown in FIG. 12(a) is thus made approximate to a view angle Q2 as shown in FIG. 12 (c).

Further, the windows 43a, 43b are formed larger than the illumination optical systems 41a, 41b to obtain a sufficient characteristic of light distribution.

Figure 12A:
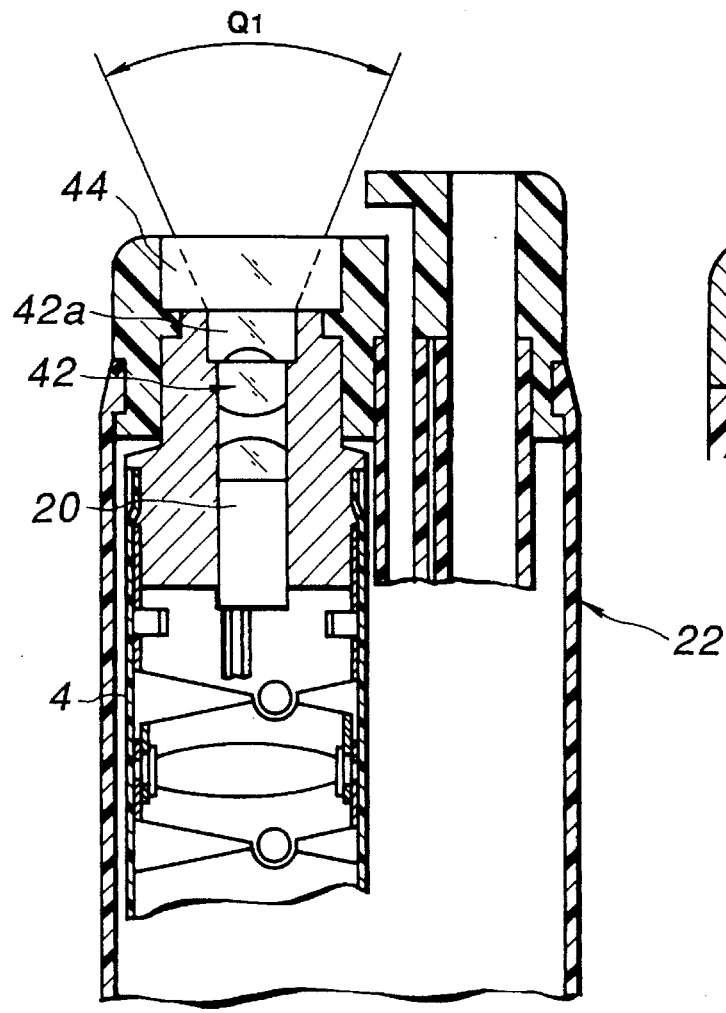
Figure 12C:
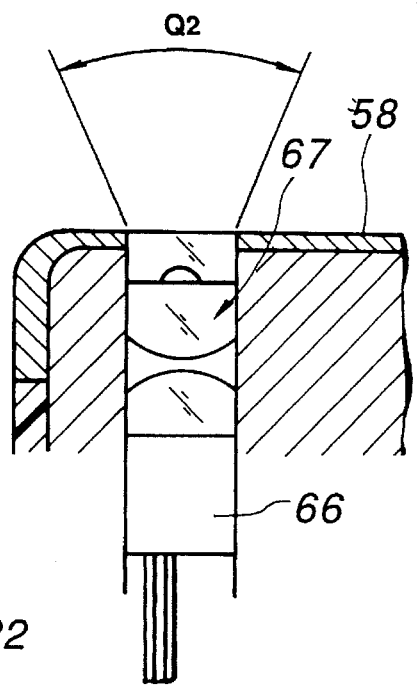

As illustrated in FIG. 12(a), let h (h=DO/2) be the maximum ray height of a first surface 42b of a front lens 42a of the objective optical lens system 42, and let ω be the half-view angle.

Further, let t be the wall thickness of the window 44, and let D be the major diameter thereof. It is also assumed that g is the spacing between the first surface 42b of the front lens 42a and the window 44.

Figure 12B:
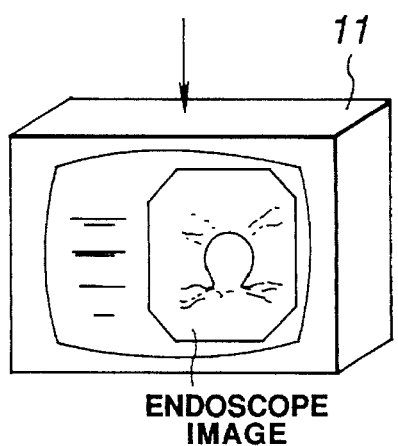
Figure 12D:
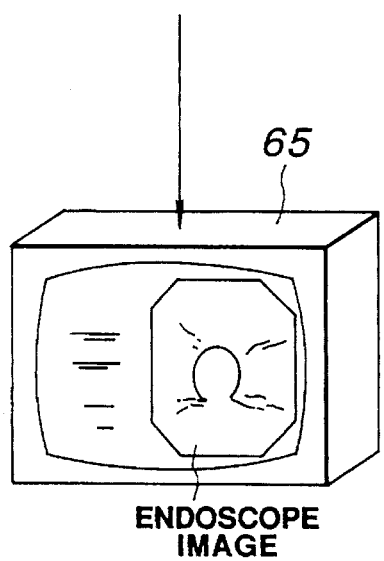

Supposing further that n is the refractive index of the window 44, the necessary minimum diameter DS of the window 44 is expressed by the following formula. Start with, an optical distance of a cover glass of the window 44 can be converted as an air layer having a distance of t/n. Hence, it can be presumed that a distance from the first surface 42b to the external surface of the window 44 is, as shown in FIG. 12(b), Given by t/n+g.

Therefore, the necessary minimum major diameter DS of the window 44 shown in FIG. 12(a) is expressed by the following formula:

$$DS = 2 \times \tan\omega \cdot (t/n + g) + 2h$$
$$= \{\tan\omega \cdot (t/n + g) + h\}$$

Namely, $DS \geq 2\{\tan\omega \cdot (t/n+g)+h\}$. It is therefore possible to ensure a view angle of a single unit of cover endoscope 4 even when fitted with the cover 3.

For instance, the cover 3 is covered on the endoscope 4 having a view angle of 100° and the first surface 2b maximum ray height of 1 mm. It is then assumed that the spacing between the first surface 42b and the window 44 is 0.5 mm, the thickness t of the window 44 is 0.5 mm, and the refractive index n is 1.51633. The necessary minimum lens major diameter DS of the window 44 is given by:

$DS \geq 2\{\tan \omega \cdot (t/n+g)+h\}$ $DS \geq 2\{\tan 100/2 \cdot (0.5/1.51633+0.5+1)$ $DS \geq 6.34$ The window 44 therefore requires the major diameter of 6.34 mm or more.

Note that the relational formula given above is established similarly in the endoscope system having a view angle peculiar to the cover endoscope.

Further, in the case of the illumination windows 43a, 43b, when making a calculation by adding an angle α, e.g., 1°~10° to the half-view angle ω, the sufficient light distribution is obtained. More specifically, a major diameter DL of each of the windows 43a, 43b is expressed such as:

$DL=2\{\tan(\omega+\alpha)\cdot(tL/n+gL)+hL\}$ where hL of the ray height of the first surface of the illumination lens, tL is the wall thickness of each of the illumination windows 43a, 43b, nL is the refractive index, and gL is the spacing between the first surface and each of the windows 43a, 43b.

The relational formula given above is satisfied, thereby obtaining substantially the same view image in the cover endoscope as that in the coverless endoscope.

Further, in accordance with this embodiment, as illustrated in FIG. 12, the same screen configuration can be acquired in the cover endoscope as that in the coverless endoscope. As depicted in FIGS. 12(b) and 12(d), a monitor image displayed on a monitor 11 in the cover endoscope is substantially the same as a monitor image displayed on a monitor 65 in the coverless endoscope system. The construction is provided so as not to cause an unfitted feeling in terms of visual sense.

Incidentally, when equalizing an image area of the image sensor in the cover endoscope to that in the coverless endoscope, it follows that a diameter of the distal end of the cover endoscope increases corresponding to a space needed for the window 44. It is therefore effective to reduce an aperture of entrance pupil in the objective optical system of the cover endoscope and make smaller a height of ray incident on the first surface than in the objective optical system of the coverless endoscope.

The following is an explanation of how the video processors both in the cover endoscope system and in the coverless endoscope system process the images in conjunction with FIGS. through 16.

Figure 14:
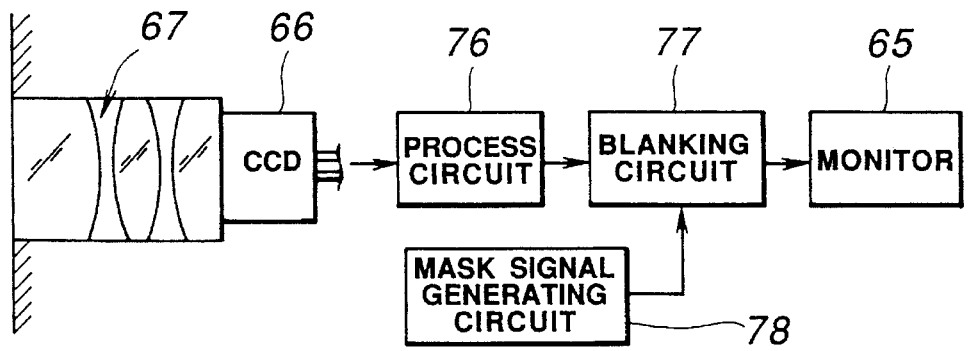

FIG. 14 is a schematic block diagram showing a coverless electronic endoscope system in a simultaneous imaging system. A video processor 62 is connected to this coverless electronic endoscope.

An unillustrated color mosaic filter is attached to the front surface of the image sensor 66 of the endoscope. A subject image formed through the objective optical system 67 of this coverless endoscope is, when received by the image sensor 65, converted into an electric signal.

The electric signal obtained by the image sensor 66 is image-processed by a process circuit 76 of the video processor 62 and thereafter transmitted to a blanking circuit 77. The blanking circuit 77 effects masking on an output signal of the process circuit 76 by use of a mask signal transmitted from a mask signal generating circuit 78. Displayed then on the monitor 65 are an endoscope image which has undergone masking and character information superimposed by an unillustrated superimpose circuit. The image is displayed on the monitor 65 as shown in, e.g., FIG. 12(d). That is, the endoscope image is not displayed fully on the screen. The image is partially displayed on one side, while the character information containing the patient information is displayed in the open space on the other side.

Figure 13:
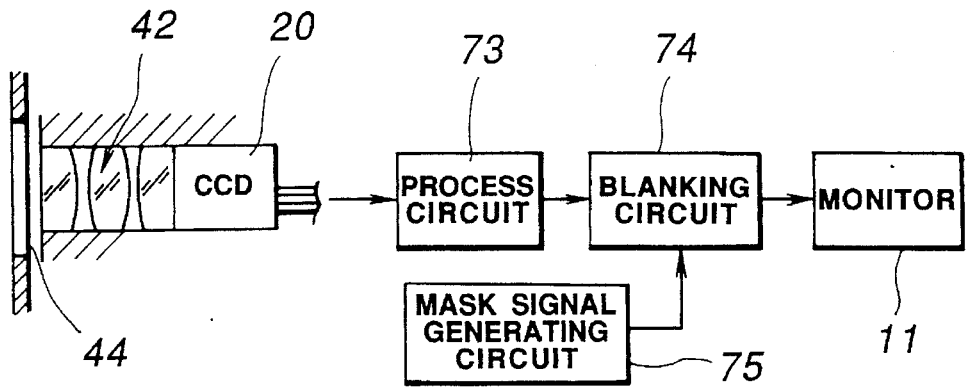

On the other hand, FIG. 13 is a schematic block diagram showing the cover electronic endoscope system in the simultaneous imaging system. The video processor 8 is connected to this cover electronic endoscope.

An unillustrated color mosaic filter is attached to the front surface of the image sensor 20 of the endoscope. A subject image formed through the objective optical system 42 of this cover endoscope is, when received by the image sensor 20, converted into an electric signal.

In the cover endoscope, the visual field may be intercepted by the cover window in some cases. The window 44 is therefore required to enlarge. If enlarged, the diameter of the distal end portion remarkably increases.

Then, this embodiment involves the use of the objective optical system and the image sensor having smaller diameters than those of the objective optical system 67 and the image sensor 66 of the coverless endoscope. To be specific, the objective optical system 42 of the cover endoscope is formed smaller in diameter than the objective optical system 67. The image sensor 20 having a smaller diameter is disposed in rear of the objective optical system 42.

Further, the electric signal obtained by the image sensor 20 is image-processed by the process circuit 73 of the video processor 8 and thereafter transmitted to the blanking circuit 74. The blanking circuit 74 effects masking on an output signal of the process circuit 73 with the aid of a mask signal transmitted from the mask signal generating circuit 75.

Displayed on the monitor 11 are an endoscope image that has undergone masking in the blanking circuit 74 and character information superimposed by an unillustrated superimposing circuit. The processing thereof is the same as in the coverless endoscope system shown in FIG. 14. Then, the mask signal generating circuit 78 generates the mask signal to obtain the same mask configuration as that in the coverless endoscope. The image is, as shown in FIG. 12(*b*), displayed on the monitor 11 in the same way with the coverless endoscope.

As discussed above, the image obtained in the cover endoscope is substantially the same as that in the coverless endoscope. Namely, the visually obtained information-, i.e., a view angle, a screen configuration, a mask, etc-is substantially the same both in the coverless endoscope system and in the cover endoscope system. Then, if superimposed, the arrangement and the configuration with respect to the endoscope image and the character information are the same.

Note that the objective optical systems 67, 42 and the image sensors 66, 20 are shown as different ones but may be, as a matter of course, identical.

Further, in the illustrative example given above, the cover endoscope system and the coverless endoscope system are constructed in different ways but are not limited to the above-mentioned, The peripheral units may be employed in common. For instance, the cover endoscope system 1 is equipped with the light source unit 7, the video processor 8 and the fluid control unit 9. However, the coverless endoscope 49 can be detachably connected to the same endoscope system 1. Both in the cover endoscope and in the coverless endoscope, all the peripheral units can be used in common.

Alternatively, some of those peripheral units are usable in common both in the cover endoscope and in the coverless endoscope.

Figure 15:
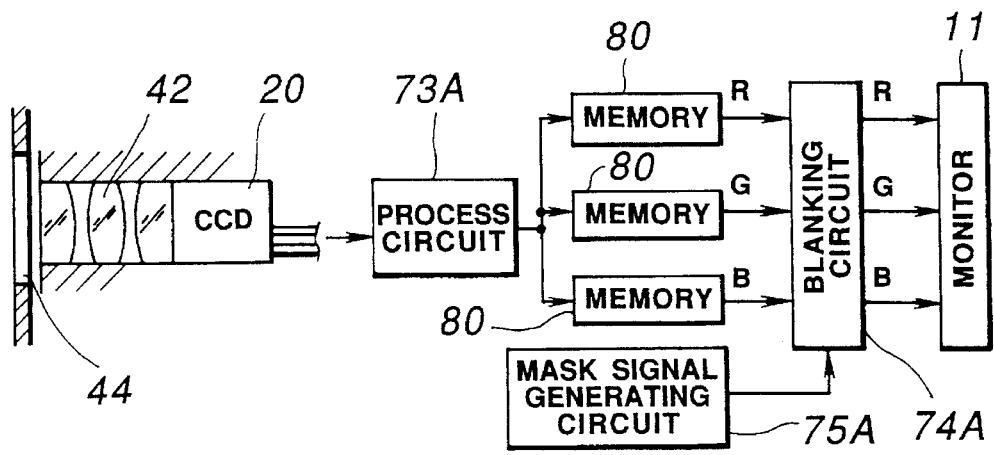
Figure 16:
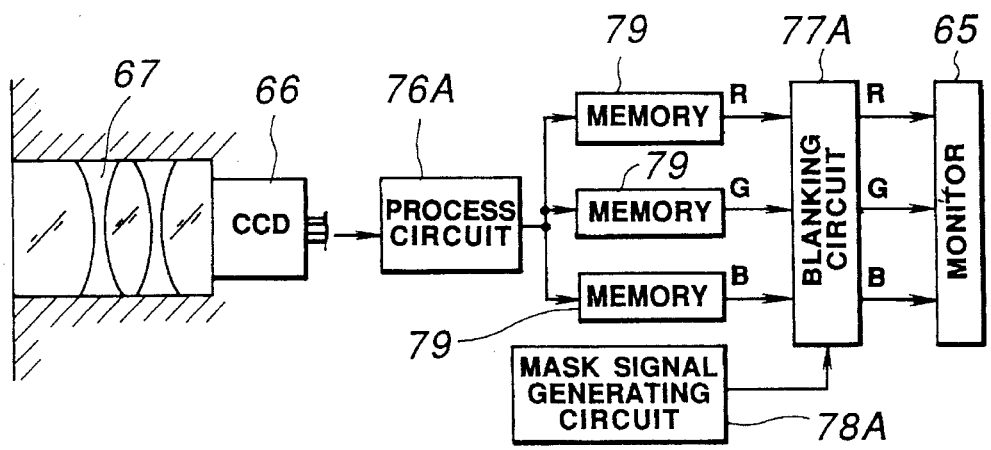

Besides, constructions shown in FIGS. 15 and 16 are related to the endoscope system in a field-sequential system.

FIG. 15 illustrates the system including the cover endoscope. On the other hand, FIG. 16 illustrates the system including the coverless endoscope. The image processing in the cover endoscope is substantially the same as the image processing on the coverless endoscope. The light source units in these two systems emit field-sequential illumination light.

Electric signals corresponding to R (red), G (green), B (blue) are obtained by the image sensor 66 of the coverless endoscope. These electric signals passing through a process circuit 76A are provided with simultaneity by means of R, G and B memories 79. Operations of a blanking circuit 77A and a mask signal Generating circuit 78A are the same as those in the above-described simultaneous system.

On the other hand, electric signals corresponding to R (red), G (green), B (blue) are obtained by the image sensor 20 of the cover endoscope. These electric signals passing through a process circuit 73A are provided with the simultaneity by means of R, G and B memories 80. Operations of a blanking circuit 74A and a mask signal generating circuit 75A are the same as those in the above-mentioned simultaneous system.

Herein, the masking is conducted in common in the two systems. There may be, however, prepared a switching device for processing to make a conversion of the image into a different one. A full screen display may be performed, wherein a view image is displayed on overall portions of the monitor.

Next, a method of installing the cover will be explained.

The installation requires two workers, i.e., a worker A in charge of installing a clean section and a worker B in charge of working in a contaminated area.

The installing method will hereinafter be explained in accordance with installing procedures. To start with, the worker A wears a sterilized glove. The worker A then holds the insert part cover section 22 and causes the hold groove 22*d* to engage with the arm 6*a* of the holding tool 6. Next, the worker B connects the dilation tube 36 to the dilation tube mouth 35 and turns ON a switch of the dilator 10. Further, the worker B inserts the insert part 14 of the cover endoscope 4 into the opening 25*a* of the endoscope insert channel 25, thereby fitting the proximal end portion of the manipulation part 12 into the mouth portion 22*a*. Further, the worker B holds the air supply conduit 26, the water supply conduit 27 and the suction conduit 28 each extending from the mouth portion 22*a* while setting these conduits along the universal cord 13. In this state, the worker A aligns an angle shaft insert port 23*d* of the manipulation part cover section 23 with the axial center of the angle knob 45. Thereafter, the connecting end 23*e* is covered around the mouth portion 22*a* and fixed thereto by the adhesive portion 23*f*. The manipulation part cover section 23 has hitherto been provided with no fixing means such as an adhesive member, a tape, etc. Accordingly, after the manipulation part 12 has been covered with the manipulation part cover section, the cover section has to be wound with the tape or the like and thus fixed. In accordance with this embodiment, however, this process is eliminated. That is, the entire fringe of the manipulation part cover section 23 is provided with the adhesive portion 23*f*, thereby facilitating the installation thereof on the manipulation part 12.

Moreover, the worker A, as illustrated in FIGS. 4(*b*) and 4(*d*), secures the angle knob 45 to the shaft protruding from the manipulation part body 12*b*. Further, after locating the universal cord cover section 24 at the cord connecting portion cover segment 23*b*, the universal cord cover section 24 is covered around the universal cord 13 to embrace even the connector 19 and fixed with the tape.

The worker B connects the air supply conduit 26, the water supply conduit 27 and the suction conduit 28 to the fluid control unit 9, thus finishing the preparation of the cover endoscope. The operator then starts an examination after removing the cover endoscope 4 from the holding tool 6.

Before being used, the cover 3 and other attachments employed in the cover endoscope system 1 are packaged in the following manner.

Figure 17:
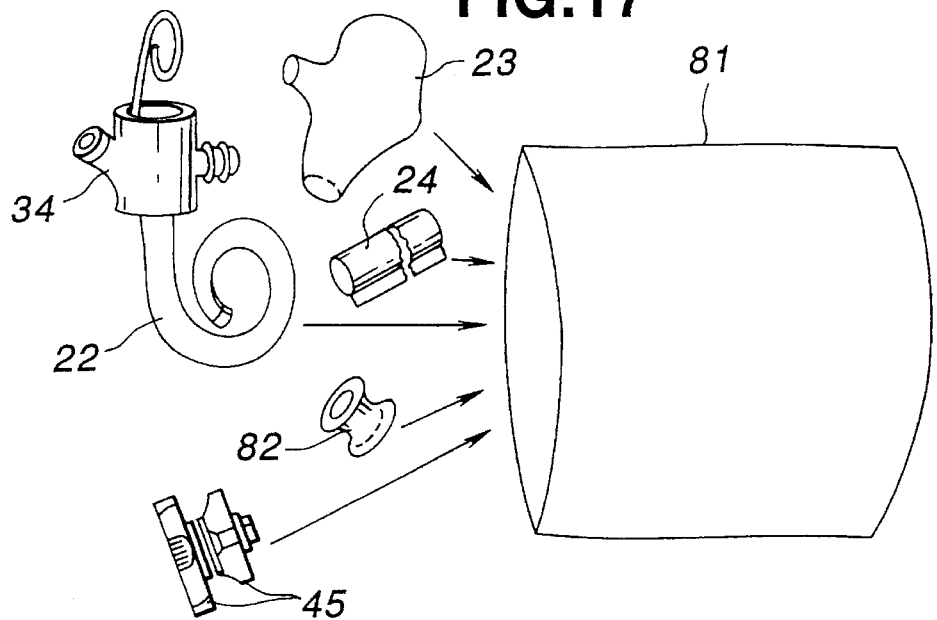

FIG. 17 illustrates a packaging member. A cover package 81 shown in FIG. 17 is formed of a porous material having holes on the order of 0.2μ or smaller enough to prevent entrance of bacterium. This package 81 is constructed to house the insert part cover section 22, the manipulation part cover section 23, the universal cord cover section 24, the angle knob 45 and a mouthpiece 82. The package 81 are after housing the cover sections is put in a sterilizer and sterilized thereby. With this sterilization, all the cover sections used in one disease case can be supplied and stored under the sterilized condition. Besides, all the parts employed in one disease case are housed therein, and hence there is no possibility a necessary cover member lacks, or any cover section fails to fit.

Figure 18:
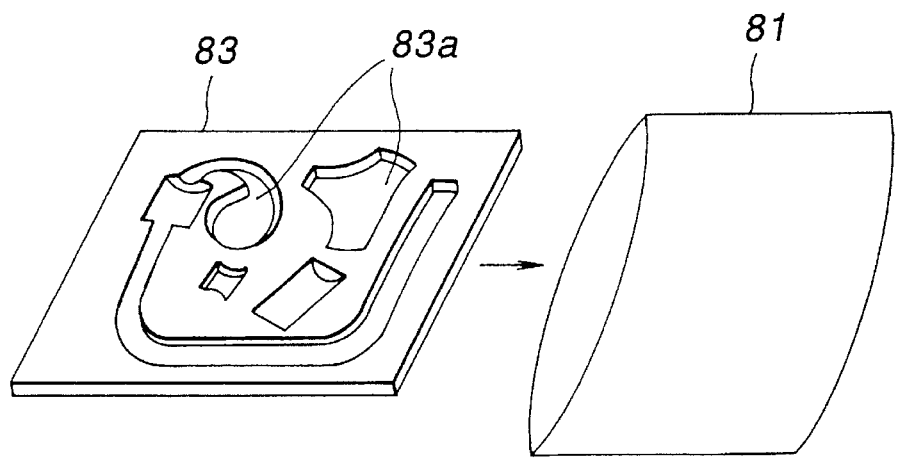

Note that this package 81 may be constructed in the following way to prevent a mistake in housing on the side of the maker. More specifically, the parts are set in a tray 83 serving as a parts setting member formed with housing spaces 83a for the respective parts shown in FIG. 18. Thereafter, the tray 83 may be housed in the package 81.

Figure 19:
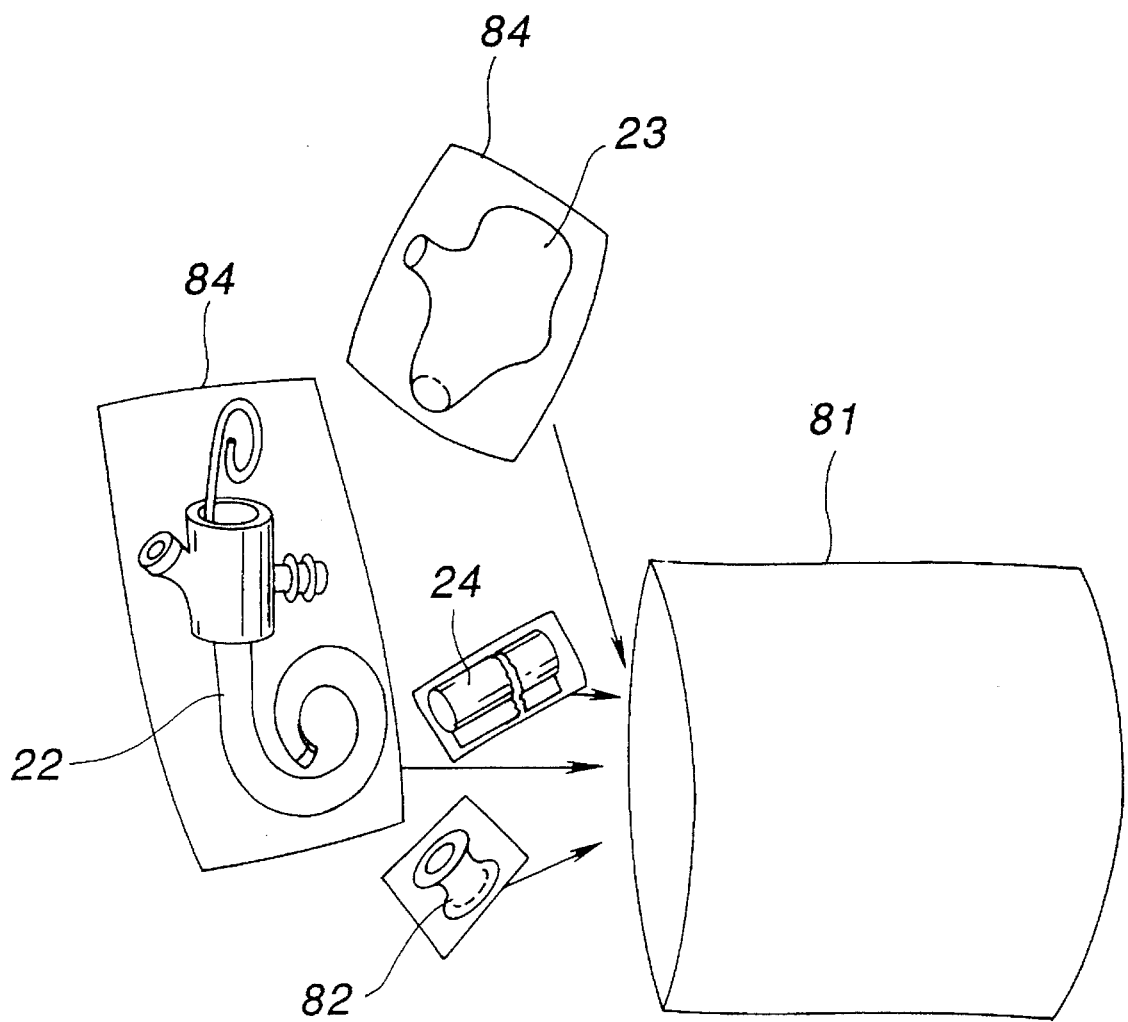

Further, as illustrated in FIG. 19, each cover section is housed in each small-sized subpackage 84. These subpackages 84 may be housed in the single package 81.

Based on the construction described above, it is feasible to prevent the examination from being impossible because of a lack of the cover sections employed in one disease case due to a mistake in arrangement or prevent the necessary cover sections from a failure in installation. Namely, the package 81 is prepared as a packaGinG member capable of keeping all the parts under the surely sterilized condition.

As discussed above, the visually obtained information-, i.e., the view angle, the screen configuration and the mask-is substantially the same both in the coverless endoscope system and in the cover endoscope system. Further, the way how the treatment tool is seen on the screen when inserting the treatment tool is substantially the same. That is, in accordance with this embodiment, the monitor images are formed substantially the same in the coverless endoscope and in the cover endoscope. No unfitted feeling is produced in the information obtained from the visual sense, whereby the well-experienced skill is not particularly needed. For example, the insert part aims at a vicinity of the target part, or a canal-endoscopic treatment tool is manipulated while seeing the monitor display. In accordance with this embodiment, however, the screen configuration is arranged in common to the coverless endoscope system, and the same manipulation feeling is also obtained. Hence, this embodiment provides no unnatural and erroneous manipulation derived from the difference in terms of manipulation feeling, and the safety can be ensured. Additionally, an oversight of the diseased part due to the difference in the screen configuration can not be induced in this embodiment.

Furthermore, this embodiment adopts such an arrangement that the manipulation factors (a configuration of the grasping portion, a position of the knob and an angle between the universal cord and the manipulation part body) of the manipulation part are adapted to those in the manipulation part of the coverless endoscope. The same manipulation feeling is thereby shared with each other. The well-experienced skill is therefore required, and a safety examination can be immediately practiced.

Figure 20:
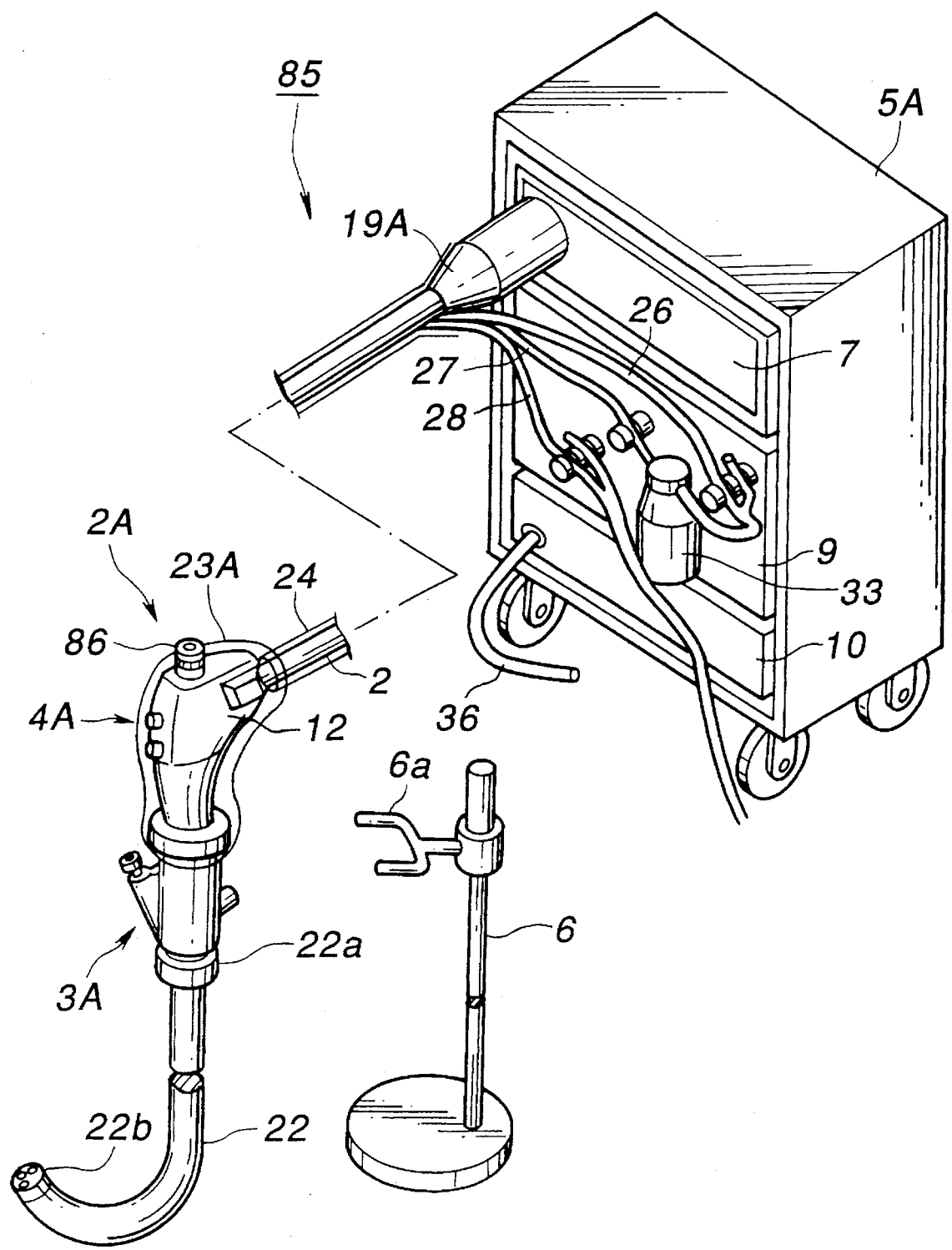
FIGS. 20 through 23 show a second embodiment of the present invention.
Figure 21:
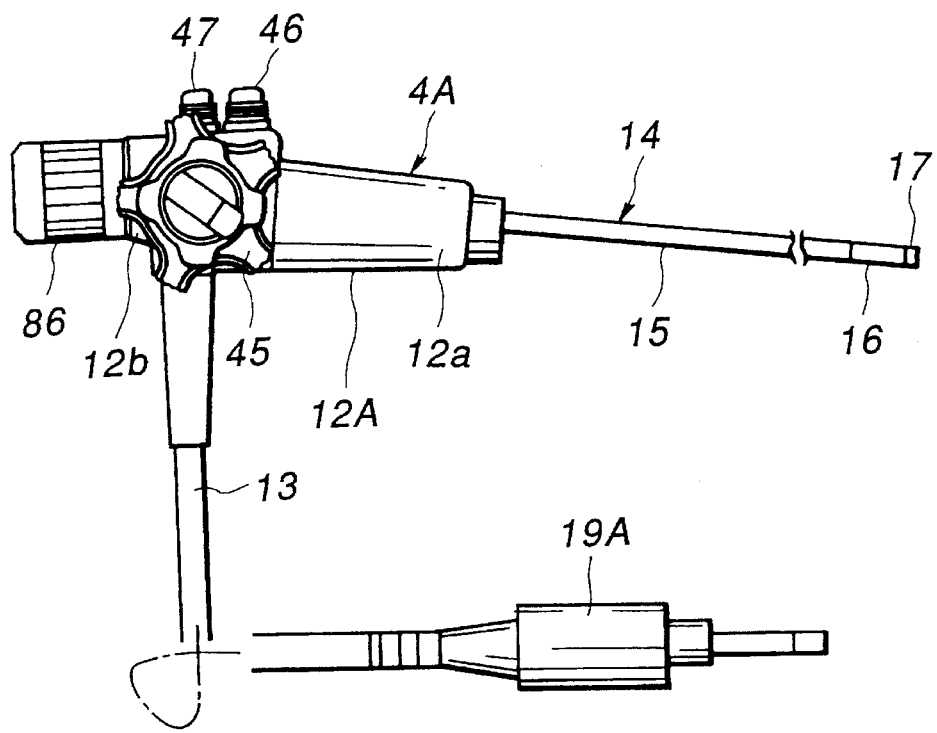
Figure 22:
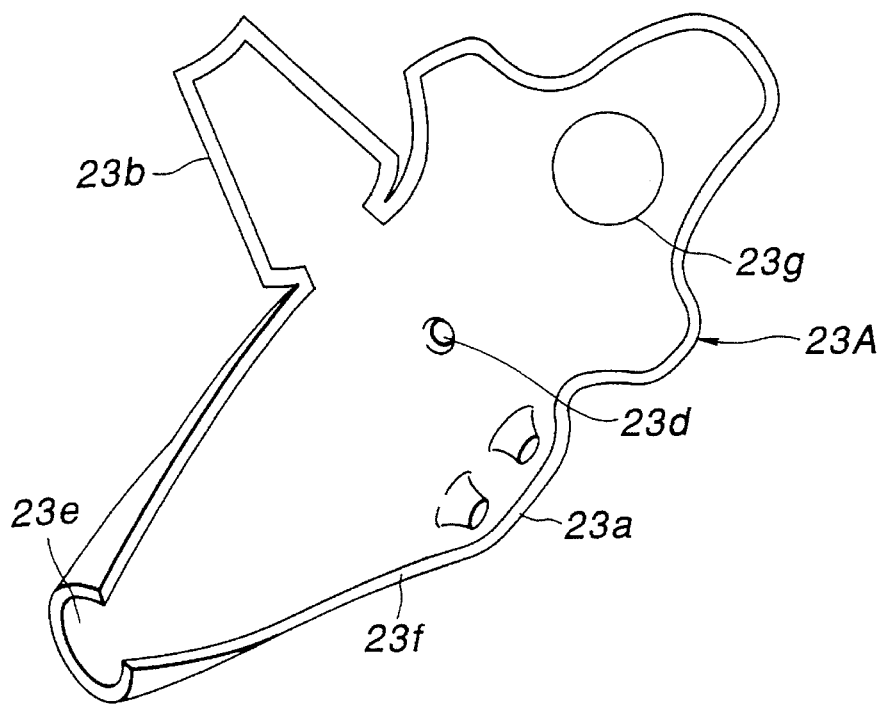
Figure 23A:
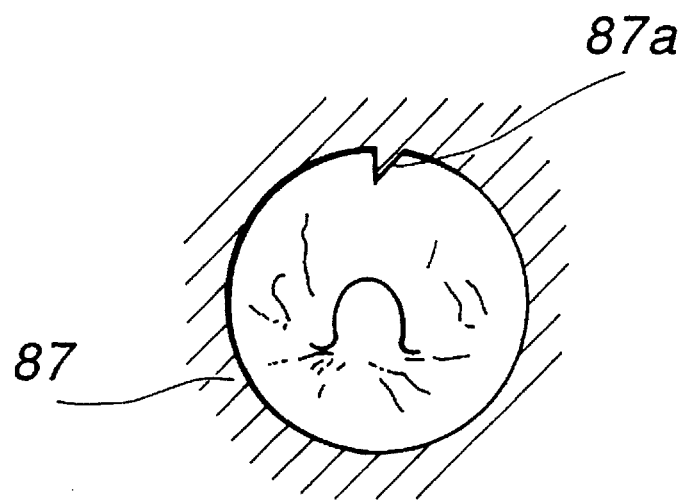
Figure 23B:
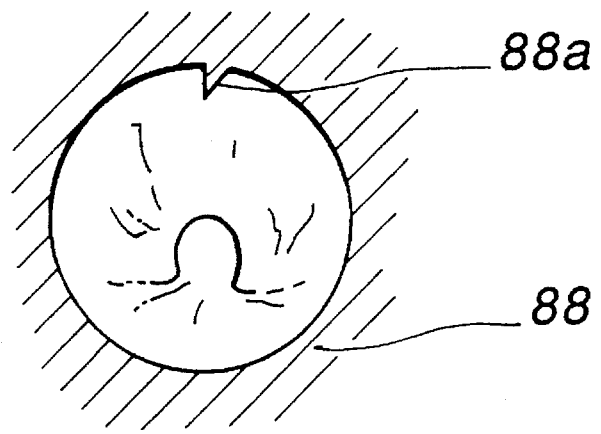

FIGS. 20 through 23 show a second embodiment of the present invention. FIG. 20 is a view illustrating an external appearance of the whole endoscope system to which the cover endoscope is connected. FIG. 21 is a view showing a profile of the cover endoscope. FIG. 22 is a view illustrating a configuration of the manipulation cover section. FIG. 23 is an explanatory view showing a view mask.

The second embodiment involves the use of an optical fiber endoscope in place of the electronic endoscope shown in the first embodiment. In others, the same components as those in the first embodiment are marked with the like symbols with an omission of explanation about the same configuration and operation.

An endoscope system 85 shown in FIG. 20 includes a cover type endoscope unit 2A consisting of a cover 3A and a cover endoscope 4A. The cover endoscope 4A is detachably connected to the endoscope system 85. At the same time, a coverless endoscope is also detachably connectable thereto.

A cart 5A houses peripheral units, e.g., the light source unit 7, the fluid control unit 9, the dilator 10, etc. The cover endoscope 4A is detachably connected to the light source unit 7. The cover endoscope 4A is fitted with the cover 3A to be covered thereon. The cover 3A is constructed of the insert part cover section 22, the manipulation cover section 23 and the universal cord cover section 24.

As illustrated in FIG. 21, the insert part 14 and the universal cord 13 are connected to the manipulation part 12A of the cover endoscope 4A. The grasping portion 12a is formed at the proximal end of the manipulation part 12A. The angle knob 45, the air/water supply control switch 46, the suction control switch 47 mounted on the manipulation part body 12b are disposed upwardly of this grasping portion 12a. Further, an eyepiece portion 86 protrudes from the near-at-hand portion of the manipulation part body 12b. An image obtained via an unillustrated optical system and image guide can be viewed through the eyepiece portion 86.

The angle knob 45 is detachably attached to the manipulation part body 12b.

The insert part cover section 22 and the universal cord cover section 24 are the same as those in the first embodiment, and their description is therefore omitted.

The manipulation part cover section 23A is constructed substantially in the same way with the manipulation cover section 23 in the first embodiment. A different point of the manipulation part cover section 23A from that in the first embodiment is, as shown in FIG. 2, to form an eyepiece portion insert port 23g from which the eyepiece portion 86 is exposed. The fringe of the manipulation part cover section 23A is, as in the first embodiment, provided with the adhesive portion 23f for facilitating the installation.

Note that the installation of the cover sections on the cover endoscope 4A is the same as that in the first embodiment and therefore omitted in its description.

FIG. 23(*a*) illustrates a configuration in a viewable range as well as a view image seen through the eyepiece portion 86. A mask member generally designated at 87 in the Figure serves as a mask means for masking, e.g., a peripheral portion in a range of visual field that is obtained through the objective optical system and the image guide. The mask member 87 is disposed between the objective optical system and the illustrated eyepiece optical system of the eyepiece portion 86, e.g., in the vicinity of the eyepiece optical system. The mask member 87 masks the peripheral portion in a substantially circular shape that typically darkens. At the same time, the mask member 87 is formed with, e.g., a substantially triangular confirmation index portion 87a partially recessed inwardly of the circular shape enough to recognize the up-and-down positions.

According to this embodiment, the view optical system, of the cover endoscope similarly takes a viewable construction as in the view optical system of the coverless endoscope. Therefore, as shown in FIG. 23(*b*), a mask 88 of the coverless endoscope is provided, and the same view image is obtained. Note that the symbol 88a in the Figure represents a confirmation index portion.

Other operations and effects are the same as those in the first embodiment, and their explanation is therefore omitted.

Note that the cover is not limited to the channeled cover described above but may include those with no channel in this embodiment.

Figure 24:
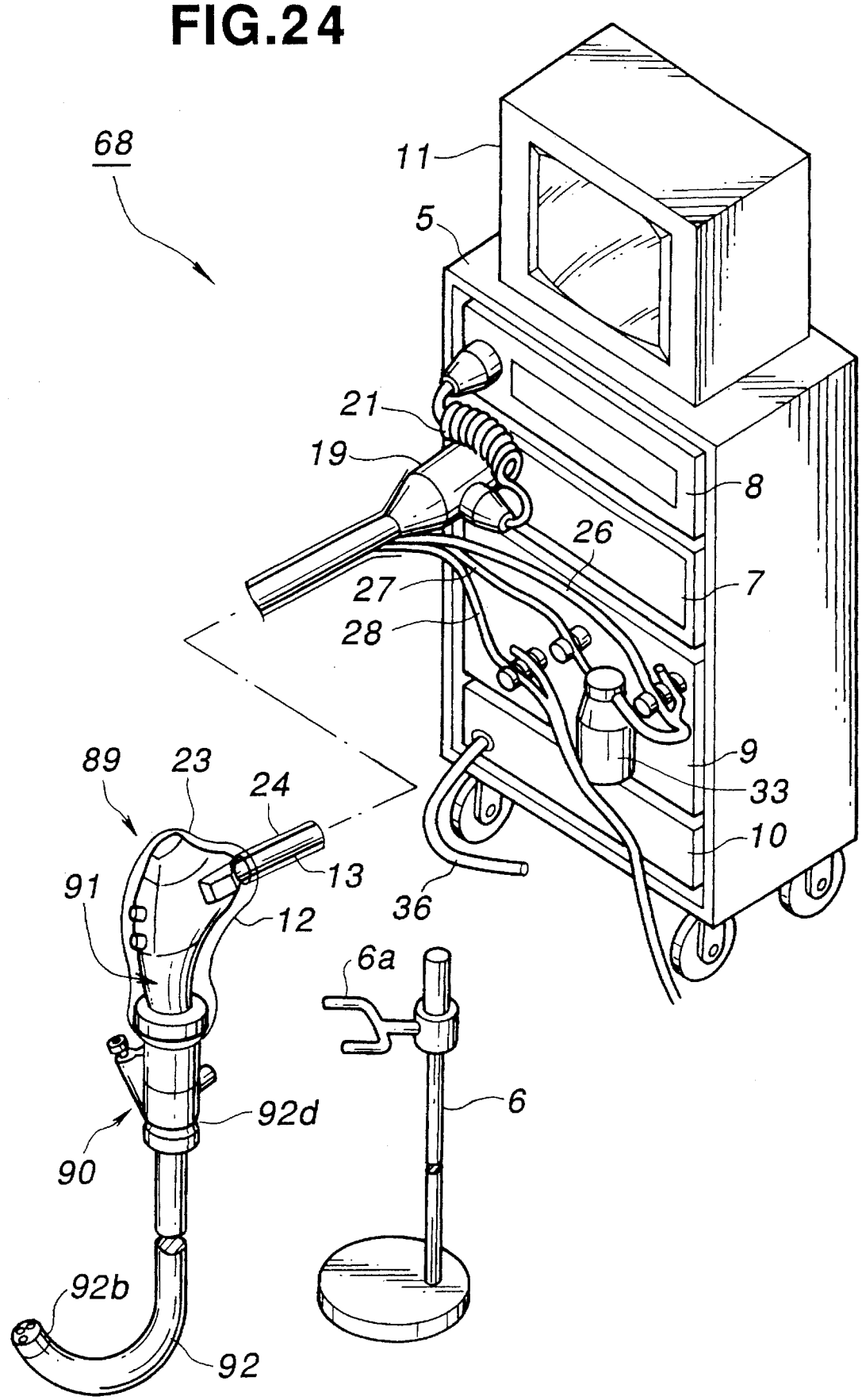
FIGS. 24 through 30 show a third embodiment of this invention.
Figure 25:
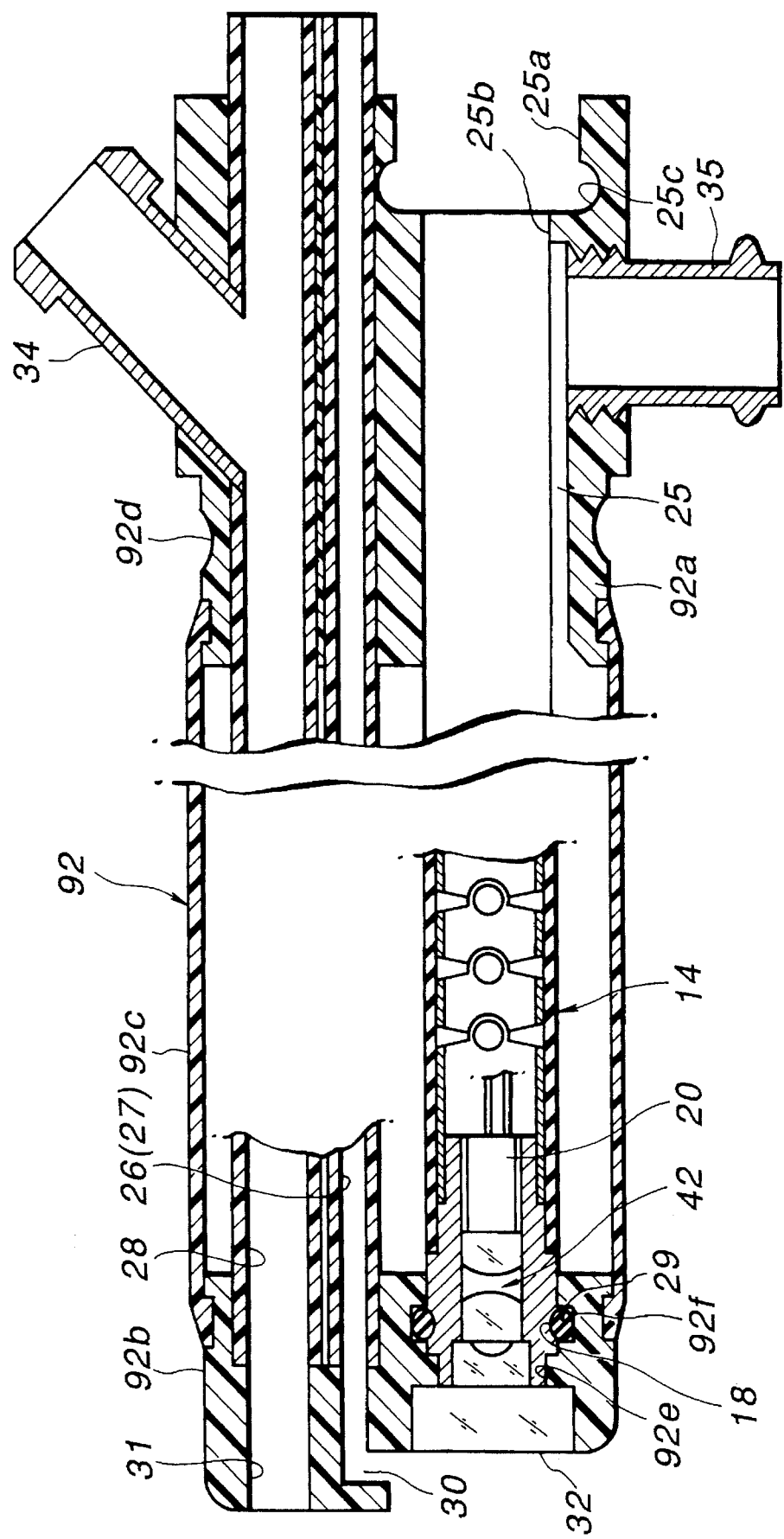
Figure 26:
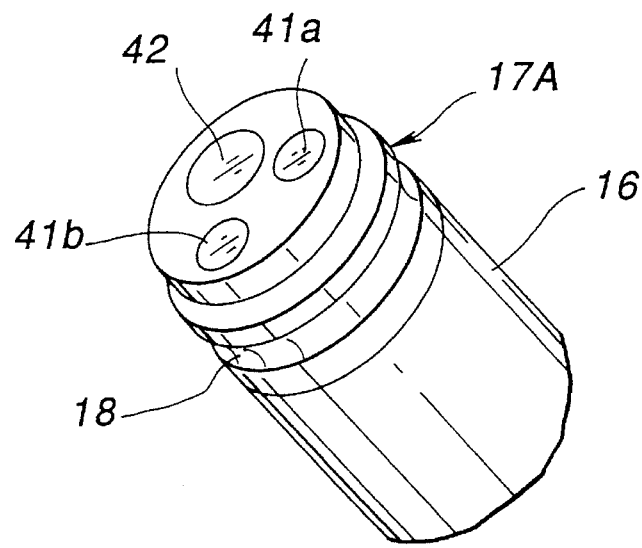
Figure 27:
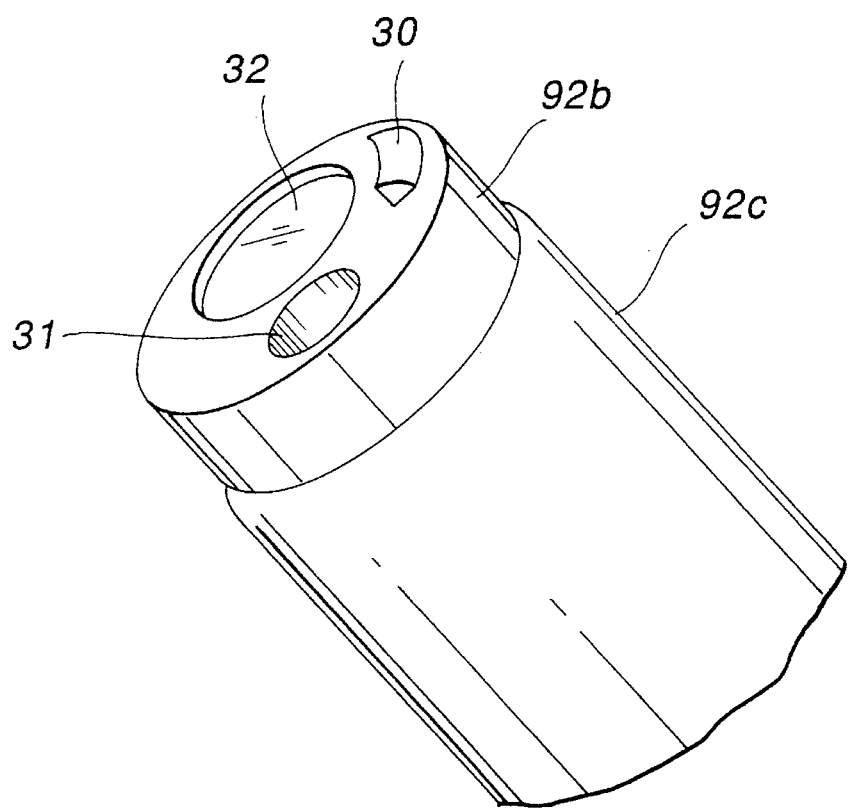
Figure 28:
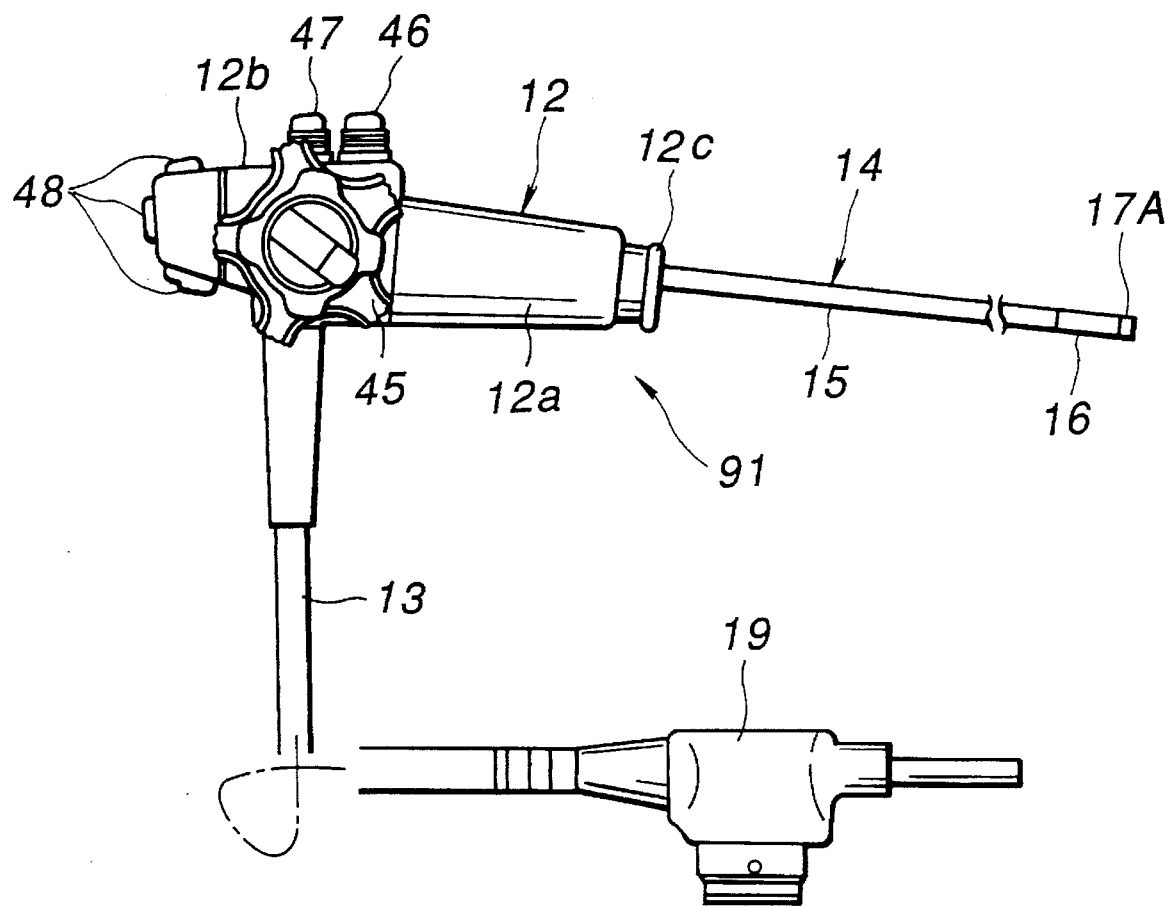
Figure 29:
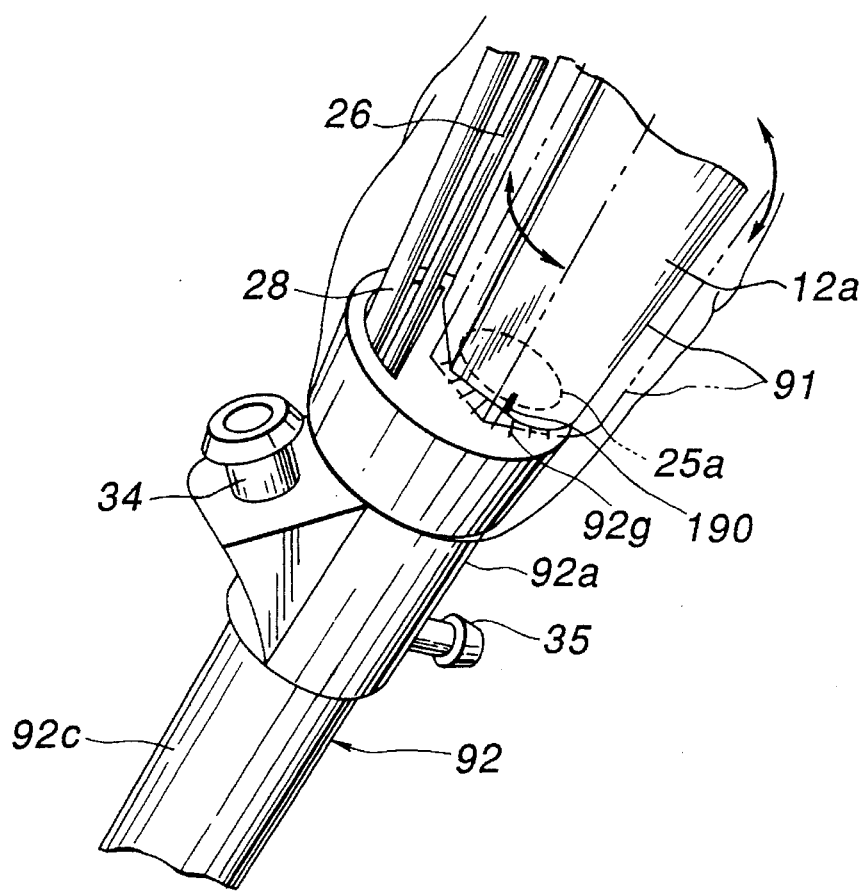

FIGS. 24 through 30 show a third embodiment of this invention. FIG. 24 is a view showing an external appearance of the whole endoscope system to which the cover endoscope is connected. FIG. 25 is a side sectional view showing the distal end part of the cover endoscope. FIG. 26 is a perspective view showing the distal end part of the cover endoscope. FIG. 27 is a perspective view illustrating a distal end of the insert part cover section. FIG. 28 is a view showing an external appearance of the whole cover endoscope. FIG. 29 is an explanatory view showing how the insert part cover section rotates about the endoscope. FIG. 30 is an explanatory view showing how the treatment tool aims at a target.

An endoscope system 68 shown in FIG. 24 includes a channeled endoscope cover type endoscope unit (hereinafter simply referred to as a cover endoscope unit) 89.

The cover type endoscope unit 89 comprises a combination of a channeled endoscope cover (hereinafter simply called a cover) 90 and a channeled endoscope cover endoscope (hereinafter simply called a cover endoscope) 91. The cover endoscope 89 is classified as an electronic type.

Further, the cover 90 is covered on the insert part of the cover endoscope 91, thus eliminating the necessity for cleaning and disinfection of the endoscope after an examination has been done.

The endoscope system 68 includes the cover type endoscope unit 89, the cart 5 incorporating a variety of peripheral devices connected to this cover type endoscope unit 89 and the cover holding tool 6 for holding the cover type endoscope unit 89.

The cart 5 accommodating the peripheral devices shown in FIG. 1 houses, e.g., the light source unit 7, the video processor 8, the fluid control unit 9 and the channeled endoscope cover dilator (hereafter simply called a dilator) 10. Besides, the monitor 11 is mounted on the top plate of the cart 5.

The light source unit 7 emits illumination light towards the cover endoscope 91 of the cover type endoscope unit 89. Further, the video processor 8 connected to the electronic type cover endoscope 91 converts an electric signal transmitted from the same endoscope 91 into a standard video signal. The video processor 8 outputs the video signal to the monitor 11. The monitor 11 displays, on receiving the video signal, an endoscope image thereon.

Further, the fluid control unit 9 supplies the air and water via conduits provided inwardly of the cover 90, which will be stated later. For this purpose, the fluid control unit 9 is equipped with a water supply source and an unillustrated air supply source. The conduits connected to the air and water supply sources are so controlled as to be opened and closed by means of solenoid valves.

Additionally, the dilator 10 works to feed the air into the cover 90 to dilate this cover 90. The dilation thereof facilitates an installation or a removal of the cover endoscope 91 into or from the cover 90.

The cover endoscope 91 is constructed, as depicted in FIG. 28, of the manipulation part 12, the universal cord 13 extending from a side portion of this manipulation part 12 and an insert part 14 connected to this manipulation part 12. As shown in FIG. 28, the insert part 14 of the cover endoscope 91 is constructed of, sequentially from a proximal end of the manipulation part 12 toward its distal end, the flexible tube portion 15, the bendable portion 16 and a hard distal end portion 17A.

The insert part 14 of the cover endoscope 4 having a small diameter is formed in a cylindrical shape in section.

A stopper groove 18 engaging with a stopper ring which will hereafter be mentioned is cut in the outer periphery of the distal end portion 17A. Besides, the distal end portion 17A of the cover endoscope 91 is, as depicted in FIG. 26, provided with the illumination optical systems 41a, 41b and the objective optical system 42.

An outgoing end of an unillustrated light guide fiber is provided at the rear end of the illumination optical systems 41a, 41b. This light guide fiber is inserted through the insert part 14, the manipulation part 12 and the universal cord 13.

The connector 19 is provided at the end of the universal cord 13. This connector 19 is detachably connected to the light source unit 7. Then, the illumination light emitted from the light source unit 7 is led to an incident end of the light guide fiber.

As illustrated in FIG. 25, the solid-state image sensor 20 for converting an incoming optical image into an electric signal is disposed at a rear end of the objective optical system 42. The electric signal outputted from this solid-state image sensor 20 is inputted to the video processor 8 via a signal cord 21 extending from a side portion of the connector 19 shown in FIG. 24.

As depicted in FIG. 28, the proximal end of the manipulation part 12 serves as the grasping portion 12a. The manipulation part body 12b connected to the upper side of the grasping portion 12a is provided with the angle knob 45, the air/water supply control switch 46, the suction control switch 47, the function switch 48 for photographing, etc. Further, a fitting rib 12c is formed on the outer periphery of the tip of the distal end portion of the manipulation part 12. The fitting rib 12c is fitted in an endoscope insert channel of the insert part cover section that will be stated later.

The angle knob 45 is, as illustrated in FIG. 4, detachably attached to the manipulation part body 12b. The manipulation part 12 is constructed to acquire the same manipulating feeling as that in a coverless endoscope.

As illustrated in FIG. 24, the cover 90 with which the cover endoscope 91 is covered comprises an insert part cover section 92, the manipulation part cover section 23 and the universal cord cover section 24. The insert part cover section 92 of the cover 90 is covered on the insert part 14 of the cover endoscope 91. Further, the manipulation part cover section 23 of the cover 90 is covered on the manipulation part 12 of the cover endoscope 91 as well as on three lines of conduits that will be stated later. Besides, the universal cord cover section 24 of the cover 90 is covered on the universal cord 13 of the cover endoscope 91 as well as on three lines of conduits that will be mentioned later. Then, the cover endoscope 91 entirely fitted with the cover 90 is employed for an examination while being watertightly covered therewith.

Note that the cover holding tool 6 shown in FIG. 24 is constructed to take hold of, when installing the insert part cover section 92 on the cover endoscope 91, a hold groove cut in the insert part cover section 92 that will be stated later with the aid of the arm 6a thereof. The endoscope 91 can be thereby held without touching on the cover 909 with a hand. The operation is therefore sanitary and thus facilitated.

FIG. 25 is a side sectional view showing a state where the insert part cover section 92 of the cover 90 is covered on the cover endoscope 4.

The insert part cover section 92 is intended to isolate the insert part 14 of the cover endoscope 91 from the external environment. This insert part cover section 92 is formed in an elongate shape. An endoscope manipulation part fixing mouth portion (simply called a mouth portion) 92a on the near-at-hand side and a distal end portion 92b are each formed of a hard material, e.g., a resin. Further, a mid-part between the mouth portion 92a of the insert part cover section 92 and the distal end portion 92b thereof is covered with an insert part cover sheath 92c composed of a flexible material. The insert part cover sheath 92c is formed to have a wall thickness on the order of 0.1 mm~1 mm.

Moreover, the insert part cover section 92 is internally formed with the endoscope insert channel 25 enough to insert the insert part 14, the air supply tube 26, the water supply tube 27 and the suction tube 28.

On the side of the proximal end of the endoscope insert channel 25, the opening 25a for inserting the insert part 14 is formed in the mouth portion 92a. Further, the airtight fitting portion 25b is formed inwardly of the opening 25a of the endoscope insert channel 25. The proximal end of the endoscope manipulation part 12 is fitted in the opening 25a of the endoscope insert channel 25. Besides, the airtight fitting portion 25b is formed to have a diameter enough to be tightly fitted to the endoscope insert part 14. A fitting groove 25c engaging with the fitting rib of the cover endoscope 91 is formed between the opening 25a and the airtight fitting portion 25b. Further, the endoscope insert channel 25 is closed at the distal end portion 92b. The insert part 14 of the cover endoscope 4 is isolated airtightly from the external environment.

A hold port 92e which contacts and is fitted to the distal end portion 17A of the cover endoscope 91 is formed in the distal end portion 92b on the side of the distal end of the endoscope insert channel 25. A hold groove 92f for holding the stopper ring 29 is cut in the inner periphery of the hold port 92e in the vicinity of the distal end of the endoscope insert channel 25. Then, this stopper ring 29 is fitted in the stopper groove 18 of the endoscope, thus regulating a movement of the endoscope insert part 14 in the axial direction. On the other hand, the endoscope 91 and the endoscope insert channel 25 of the cover are rotatable.

The distal end portion 92b of the insert part cover section 92 is, as illustrated in FIG. 27, formed with a transparent window 32 at the distal end of the endoscope insert channel 25. This window 32 is formed wider than all of the illumination optical systems 41a, 41b and the objective optical system 42 of the cover endoscope 91 and disposed in face-to-face relationship thereto.

Further, the distal end portion 92b of the insert part cover section 92 is formed with an air (or water) supply nozzle 30 opened toward the window 32 and an opening (outlet for the treatment tool) 31 as well. The air (or water) supply nozzle 30 connectively communicates with the air supply tube 26 (or water supply tube 27). The opening 31 also connectively communicates with the suction tube 28.

Additionally, the air supply tube 26, the water supply tube 27 and the suction tube 28 extend from the mouth portion 92a further towards the near-at-hand side. The ends portions thereof are each opened. As depicted in FIG. 24, the air supply tube 26 connectively communicates with an unillustrated air supply source of the fluid control unit 9. Further, the water supply tube 27 connectively communicates with the air supply source via the water supply tank 33 serving as a water supply source. Still further, the suction tube 28 connectively communicates with an unillustrated suction source as well as with an unillustrated suction bottle.

As shown in FIG. 25, the treatment tool insert port 34 and the dilation tube mouth 35 are formed protrusively from the sides of the mouth portion 92a. The dilation tube mouth 35 has its internal conduit communicating with the endoscope insert channel 25. The dilation tube 36 connected to the dilator 10 is detachably connected to the dilation tube mouth 35.

The treatment tool insert port 34 protrudes backward in the axial direction of the insert part cover section 22. An internal conduit of the treatment tool insert port 34 is opened at its protruded end and communicates with the suction conduit 28 at the other end thereof. That is, the suction conduit 28 serves as a conduit of the treatment tool channel on the side of its distal end.

Cut also in the side outer periphery of the mouth portion 92a is a hold groove 92d engaging with the arm 6a of the cover holding tool 6 when holding the insert cover section 92.

Next, a configuration of the manipulation part 12 of the cover endoscope 4 will be described.

The grasping portion 12a of the cover endoscope 91 is formed so that a size and a shape thereof are, when covered with the manipulation part cover section 23, substantially identical with those of the grasping portion of the coverless endoscope.

Further, the angle knob 45 has a size and a shape that are substantially identical with those of the angle knob 53 of the coverless endoscope. Based on the construction described above, the manipulation part 12 of the cover endoscope 4 obtains the same manipulation feeling as that in the coverless endoscope.

Further, a scale 92g is, as shown in FIG. 29, formed in the vicinity of the opening 25a of the insert part cover section 22. On the other hand, an index 190 is formed on the side portion at the distal end of the grasping portion 12a of the cover endoscope 91. It is possible to recognize a positional relationship between the endoscope 91 and the treatment tool outlet 31 of the insert part cover section 22 from a position of the index 190 with respect to the scale 29.

Note that the manipulation cover section 23 and the universal cord cover section 24 of the cover 90 are constructed in the same way as that shown in FIGS. 8 and 9, and their explanation is therefore omitted.

Next, a method of installing the cover will be explained.

The installation requires two workers, i.e., the worker A in charge of installing a clean section and the worker B in charge of working in a contaminated area.

The installing method will hereinafter be explained in accordance with installing procedures. To start with, the worker A wears a sterilized glove. The worker A then holds the insert part cover section 92 and causes the hold groove 92d to engage with the arm 6a of the holding tool 6. Next, the worker B connects the dilation tube 36 to the dilation tube mouth 35 and turns ON a switch of the dilator 10. Further, the worker B inserts the insert part 14 of the cover endoscope 4 into the opening 25a of the endoscope insert channel 25, thereby fitting the proximal end portion of the manipulation part 12 into the mouth portion 92a. At this time, the endoscope distal end portion 17A is inserted till it contacts the tip of the hold port 92e of the insert part cover section 92. The installation is thus completely done. In this state, the stopper groove 18 of the endoscope engages with the stopper ring 29. The fitting rib 12c of the endoscope is also fitted in the fitting groove 25c. The engagements thereof work to regulate the movement of the cover endoscope 91 in the axial direction. While on the other hand, the insert part cover section 92 and the cover endoscope 91 are rotatable in the peripheral direction.

Incidentally, the arrangement of the conduits 26, 27, 28 each extending from the mouth portion 92a is the same as that in the first embodiment. The angle knob 45 is attached the same. The manipulation part cover section 23 and the universal cord cover section 24 are installed also in the same manner. The explanation thereof is therefore omitted.

The worker B connects the air supply conduit 26, the water supply conduit 27 and the suction conduit 28 to the fluid control unit 9, thus finishing the preparation of the cover endoscope. The operator then starts an examination after removing the cover endoscope 4 from the holding tool 6.

FIG. 29 illustrates the portions vicinal to the proximal end of the manipulation part 12 when completely fitted with the cover 3.

In the installation completed state described above, the stopper ring 29 of the distal end portion engages with the stopper groove 18; and the fitting rib 12c is fitted in the fitting groove 25c. Further, the endoscope insert part 14 takes the cylindrical shape. Hence, as illustrated in FIG. 29, the insert part cover section 92 is rotatable about the cover endoscope 91. The position of the treatment tool outlet 31 is thereby adjustable in the direction of visual field to which the manipulator is accustomed.

Moreover, it is possible to recognize the positional relationship between the direction of visual field of the endoscope and the treatment tool outlet 31 from the relation of the scale 92g versus the index 190. This relationship has been known when the endoscope 91 was initially fitted with the cover section 92 and also recognizable from even the rotation described above.

Figure 30A:
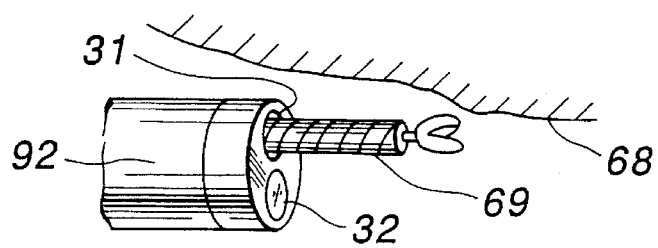
Figure 30B:
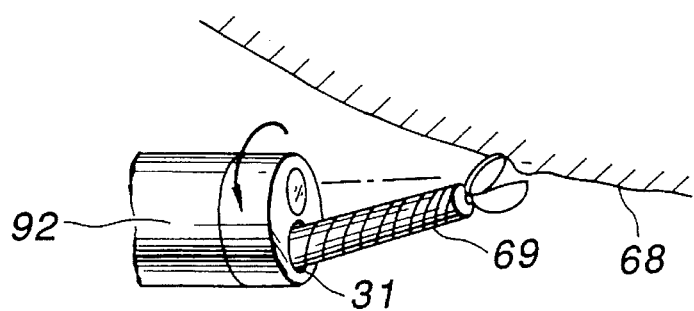

The bendable portion 16 of the endoscope 91 is freely bendable. As shown in FIG. 30(a), however, a somatic wall 68 is substantially parallel to the covered insert part 14. Besides, if very close to the somatic wall 68, it is difficult to perform the bending manipulation well. Namely, an aiming performance of the treatment tool 69 worsens so much. Accordingly, the aiming performance can be improved by separating the treatment tool output 31 from the somatic wall 68 as much as possible. Then, in this embodiment, as shown in FIG. 30(b), the insert part cover section 92 is rotated about the cover endoscope 91. The somatic wall 68 is thus spaced apart from the treatment tool outlet 31, thereby enhancing the aiming performance at a diseased part 57. For this reason, the living body examining efficiency can be further ameliorated.

Further, in accordance with this embodiment, the treatment tool such as a forceps can be adjusted to protrude in the direction of conventionally-accustomed visual field. The treatment such as a living body examination can be effected safely. Further, in accordance with this embodiment, even if the conventional cover endoscope is incapable of the treatment, the living body examining capability can be improved by a trace adjustment of the protruded position of the treatment tool by rotating the insert part cover section. In addition, the relationship between the direction of the visual field and the protruded position of the treatment tool can be always recognized with the aid of the scale 92 in combination with the index 190 in this embodiment. There is also no possibility to misjudge the protruded position of the treatment tool.

FIG. 31 is a view depicting a configuration of a modified example of this embodiment.

The cover section is rotated freely through 360° in the embodiment discussed above. In this modified example, however, a rotational quantity is properly regulated. Note that the same components as those in the embodiment described above are marked with the like symbols, and the explanation thereof is therefore omitted. Only different points will be described.

Rotation regulating portions 86, 86, 89 are, as shown in FIGS. 31(a) and 31(b), protrusively formed in the hold port 92e of the distal end portion 92b and at the tip of the insert part 14. With this construction, it is possible to prevent a twist of the suction conduit 28 due to a limitless rotation within the insert part cover section 92. A damage to the conduit is thereby prevented to provide the safety.

Incidentally, the insert part cover section 92 may be rotated about the endoscope 91 after inserting a stylet for rotation into the treatment tool channel. The styler employed herein is, it is assumed, formed of a material having a hardness equal to or greater than the generally used treatment tool. The rotary force is thereby sufficiently transmitted to the distal end of even the soft insert part cover section. The insert part cover section can be freely rotated about the endoscope.

FIG. 32 illustrates a package 81A of the insert part cover section 92.

The package 81A is constructed to surely sterilize the cover 90, especially, the insert part cover section 92 that directly contacts the somatic interior.

The package 81A is composed of a porous high polymer material or paper. The package 81A is formed with holes on the order of 0.2 mm enough to prevent the permeation of bacterium. By the way, a gas sterilization using a gas such as ethylene oxide or the like widely spreads for sterilizing the medical supplies. In this gas sterilization, however, the gas does not touch on an overlapped portion of sterilized substances. This overlapped portion can not be often sterilized. This package 81A is contrived so as not to overlap the cover 90, particularly, the insert part cover section 90. A tray 93 housed in the package 81A is formed of a porous high polymer material or paper to prevent the permeation of bacterium.

A guide groove 93a is cut in the tray 93 so as not to overlap the insert part cover section 92. The insert part cover section 92 is set along the guide groove and housed in the package 81A which is then sealed. Packing is thus completed. The gas sterilization is conducted in this state, with the result that the gas contacts the overall cover. The sufficient sterilization is thereby attained. Note that guide grooves may be formed as the guide groove 93a in the manipulation part cover section 23 as well as in the universal cord cover section 24.

Further, a guide groove may be also cut in the package 81A itself. In this instance, the tray 93 is not required, and an inexpensive package can be offered.

Figure 33:
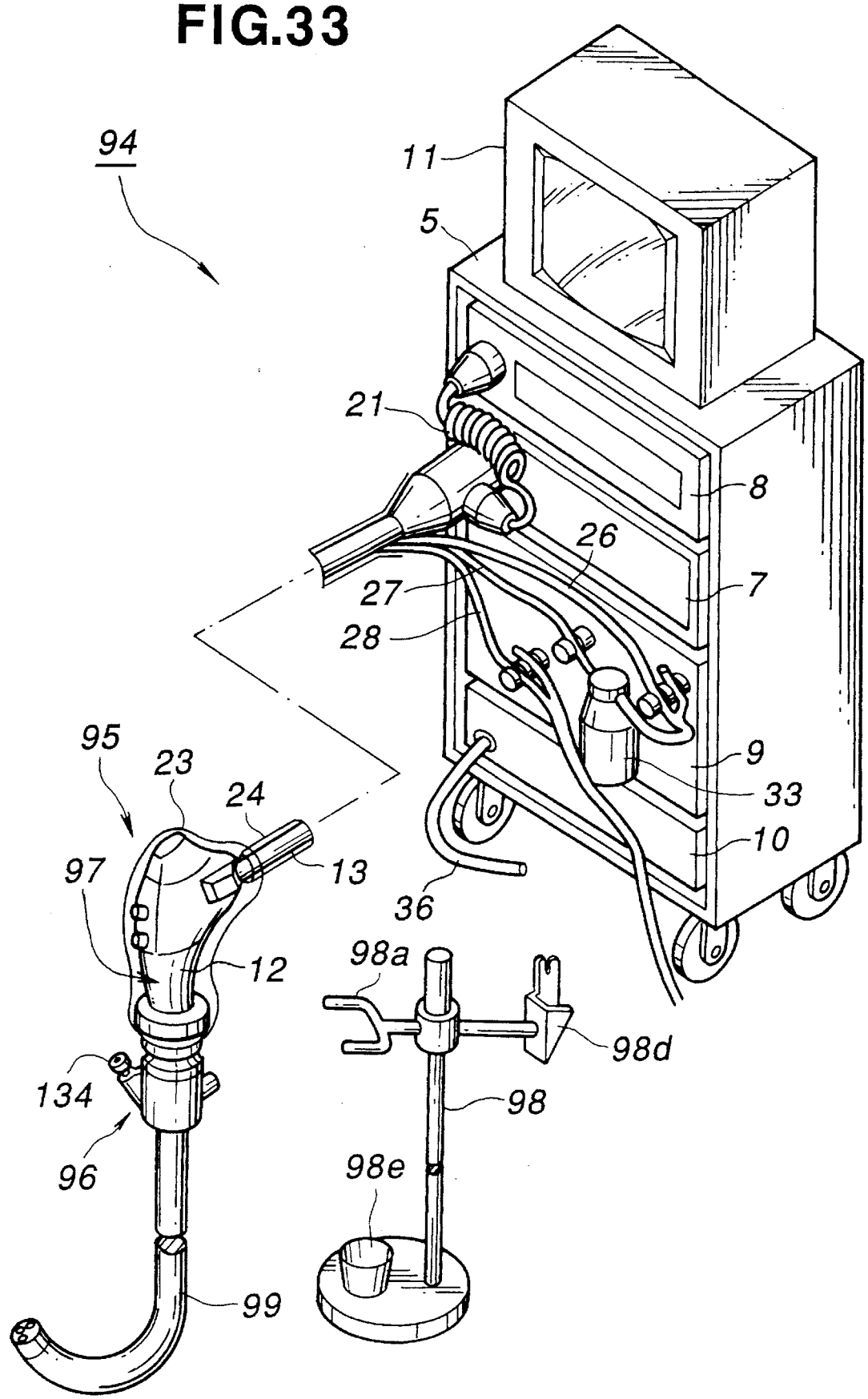
FIGS. 33 through 41 show a fourth embodiment of this invention.
Figure 34:
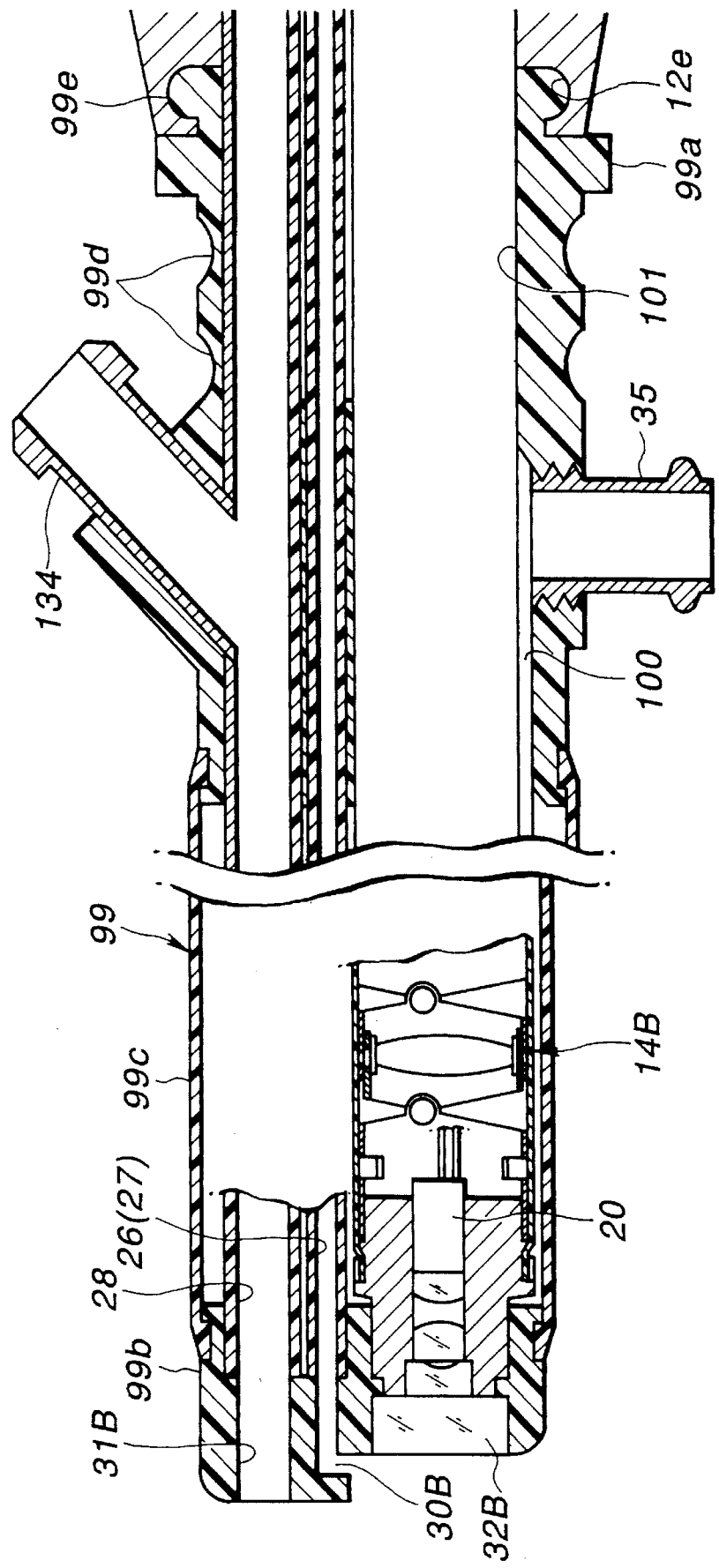
Figure 35:
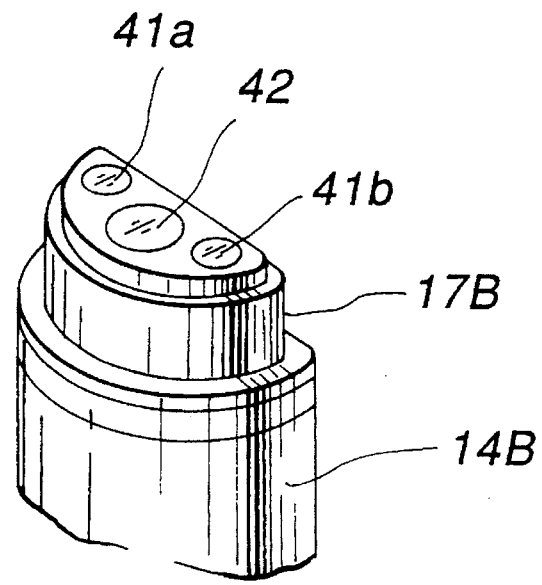
Figure 36:
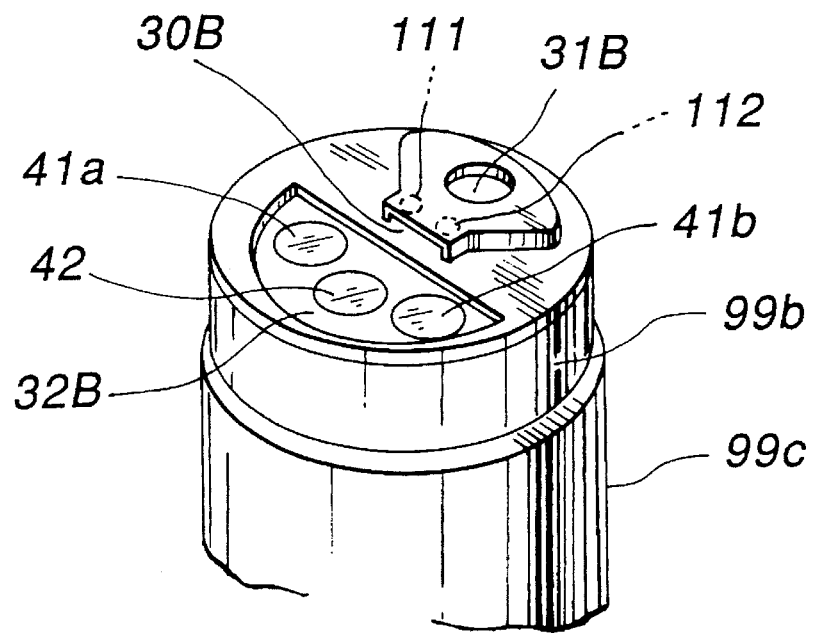
Figure 37A:
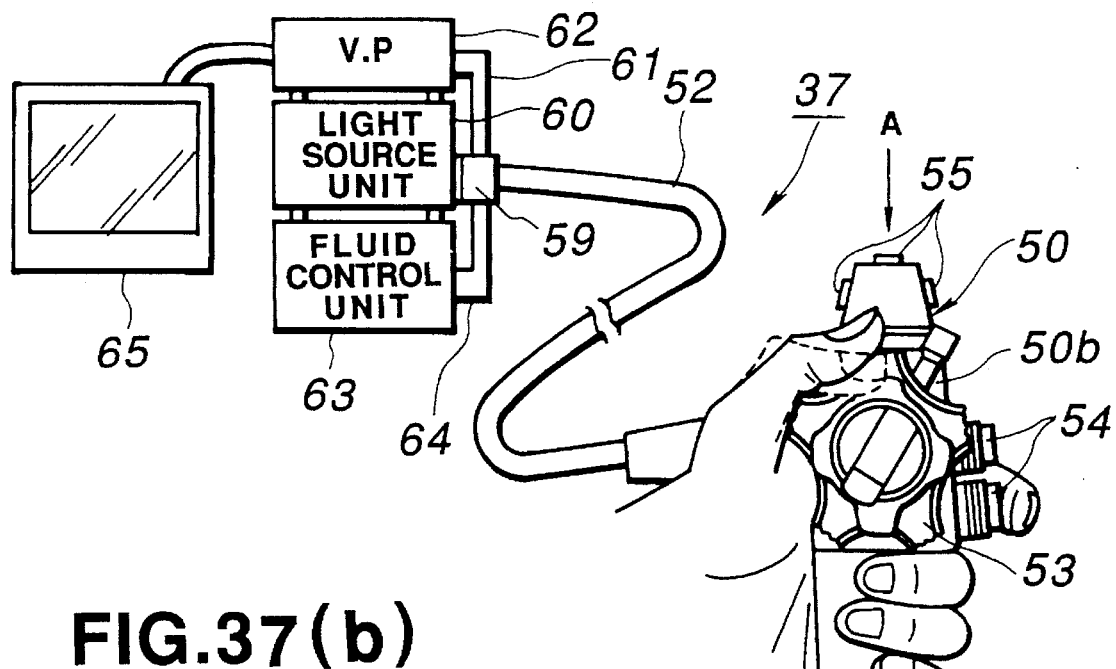
Figure 37B:
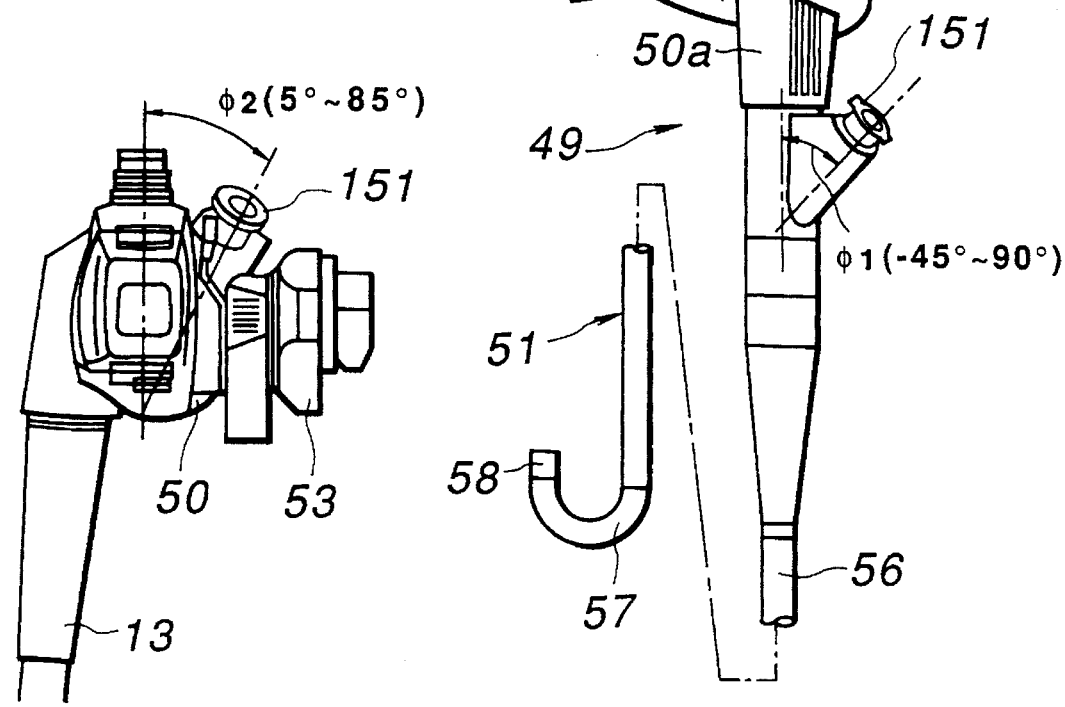
Figure 38:
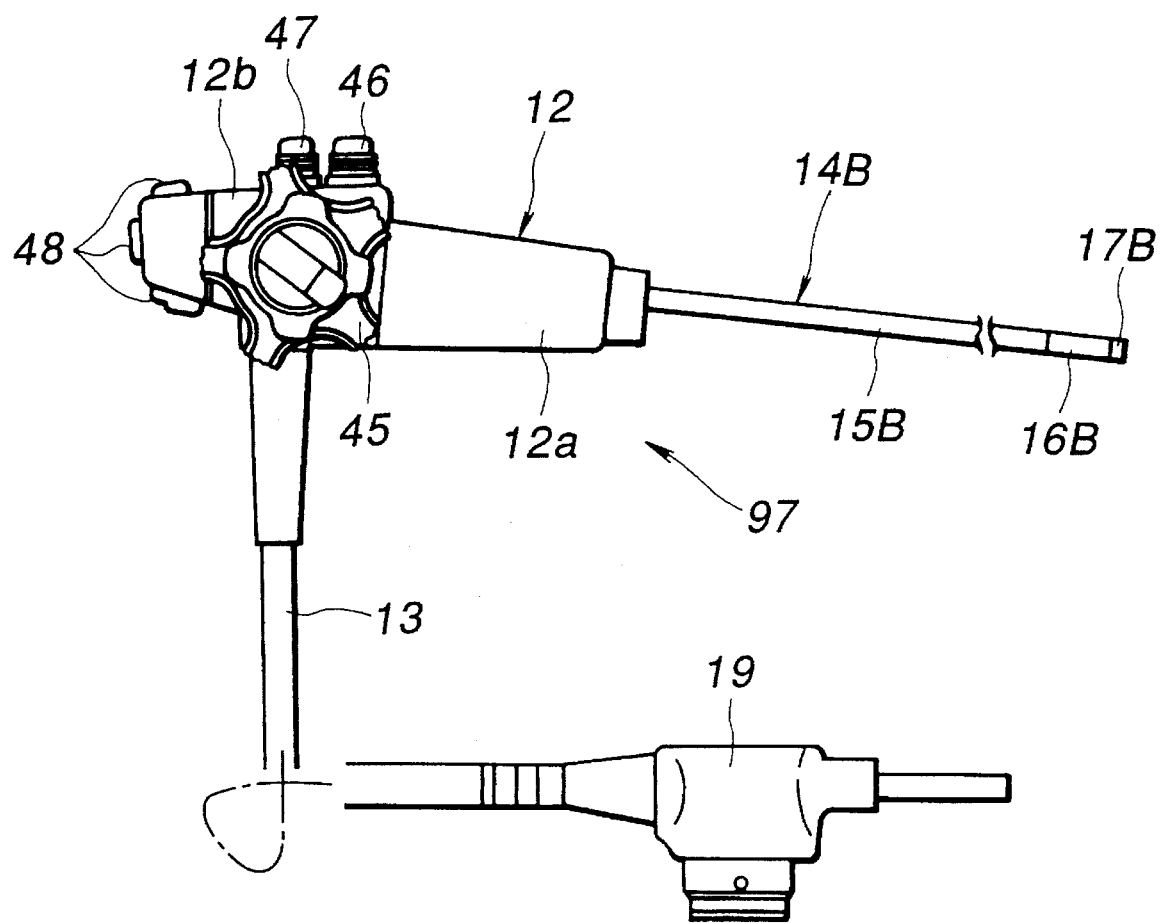
Figure 39A:
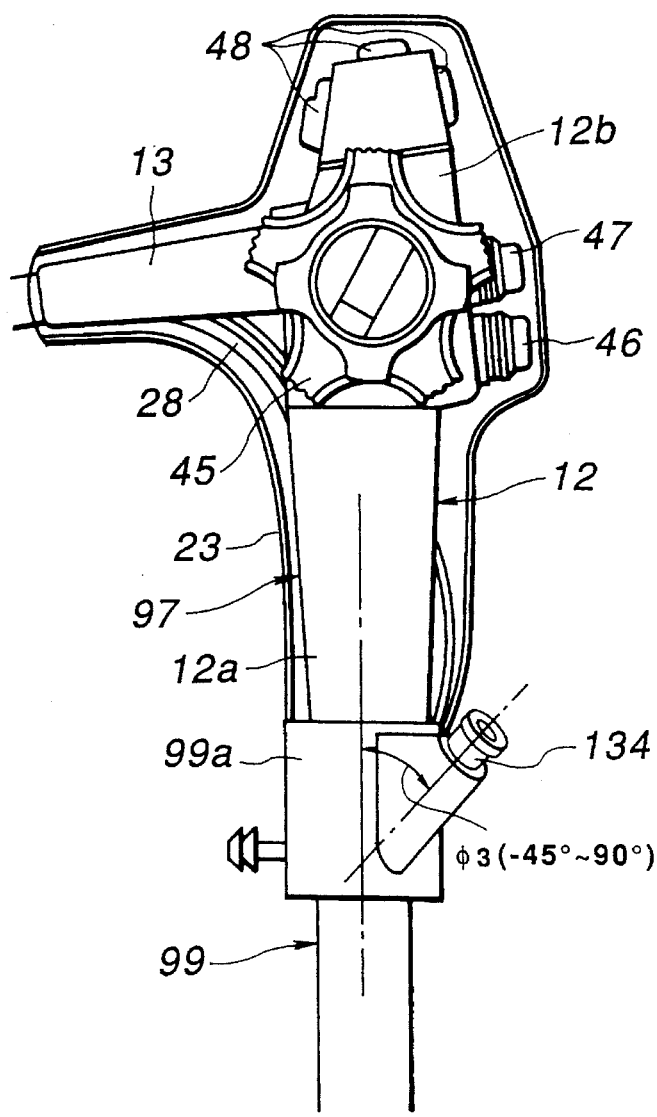
Figure 39B:
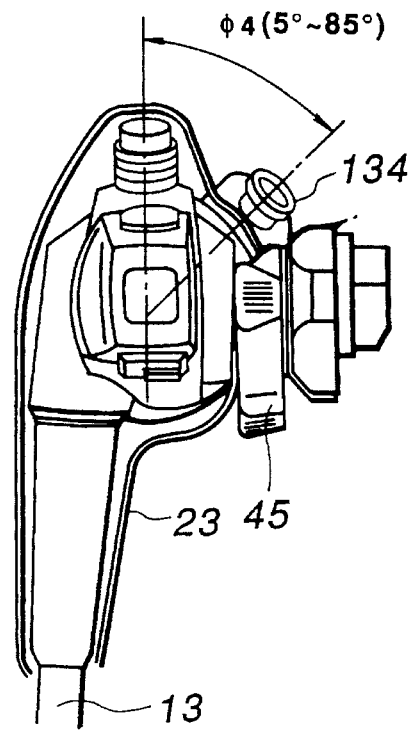
Figure 40:
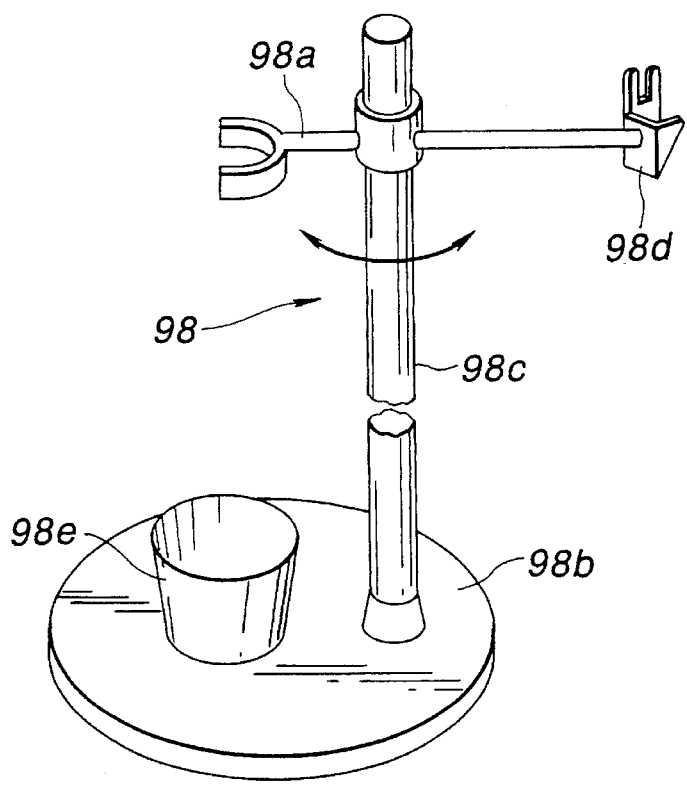
Figure 41:
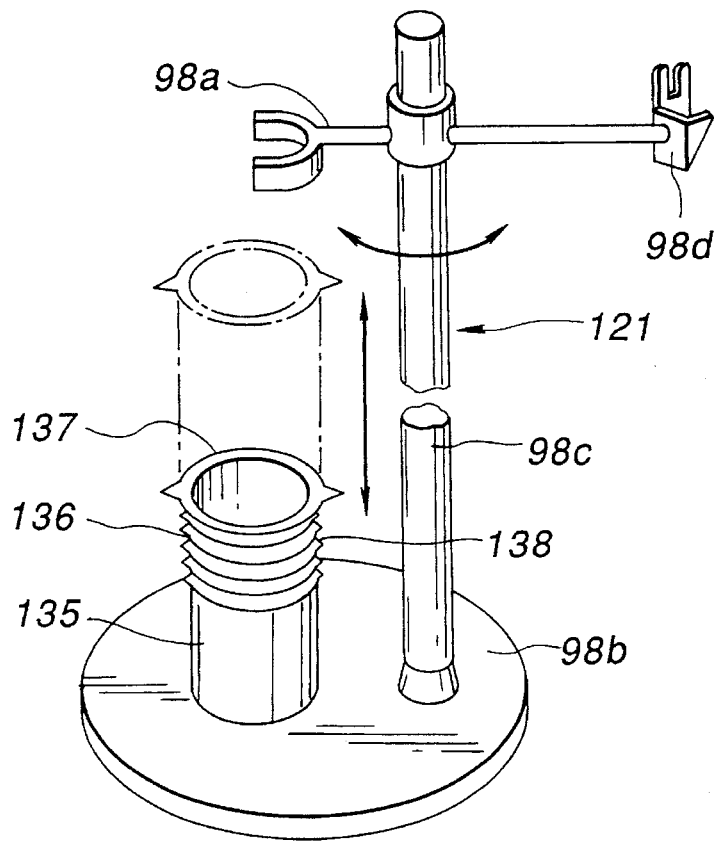

FIGS. 33 through 41 show a fourth embodiment of this invention. FIG. 33 is a view showing an external appearance of the whole endoscope system to which the cover endoscope is connected. FIG. 34 is a side sectional view showing the distal end part of the cover endoscope. FIG. 35 is a perspective view showing the distal end part of the cover endoscope. FIG. 36 is a perspective view illustrating a distal end of the insert part cover section. FIG. 37 is a view showing a construction and an external appearance of the endoscope system to which a coverless endoscope is connected. FIG. 38 is a view showing an external appearance of the cover endoscope. FIG. 39 is an explanatory view showing a fitting position in a treatment tool insert port. FIG. 40 is a perspective view illustrating a cover holding tool. FIG. 41 is a perspective view showing the cover holding tool constructed otherwise.

In an endoscope system 94 shown in FIG. 24, a channeled endoscope cover type endoscope unit (hereinafter simply referred to as a cover endoscope unit) 95 and a coverless endoscope 89 that will be state later are detachably connected thereto.

The cover endoscope unit 95 comprises a combination of a channeled endoscope cover (hereinafter simply called a cover) 96 and a channeled endoscope cover endoscope (hereinafter simply called a cover endoscope) 97. The cover endoscope 95 is classified as an electronic type.

Further, the cover 96 is covered on the insert part of the cover endoscope 97, thus eliminating the necessity for cleaning and disinfection of the endoscope after an examination has been done.

The endoscope system 94 includes the cover type endoscope unit 95, the cart 5 incorporating a variety of peripheral devices connected to this cover type endoscope unit 95 and the cover holding tool 98 for holding the cover type endoscope unit 95.

The cart 5 accommodating the peripheral devices shown in FIG. 33 houses, e.g., the light source unit 7, the video processor 8, the fluid control unit 9 and the channeled endoscope cover dilator (hereafter simply called a dilator) 10. Besides, the monitor 11 is mounted on the top plate of the cart 5.

The light source unit 7 emits illumination light towards the cover endoscope 91 of the cover type endoscope unit 89. Further, the video processor 8 connected to the electronic type cover endoscope 97 converts an electric signal transmitted from the same endoscope into a standard video signal. The video processor 8 outputs the video signal to the monitor 11. The monitor 11 displays, on receiving the video signal, an endoscope image thereon.

Further, the fluid control unit 9 supplies the air and water via conduits provided inwardly of the cover 96, which will be stated later. For this purpose, the fluid control unit 9 is equipped with a water supply source and an unillustrated air supply source. The conduits connected to the air and water supply sources are so controlled as to be opened and closed by means of solenoid valves.

Additionally, the dilator 10 works to feed the air into the cover 96 to dilate this cover 96. The dilation thereof facilitates an installation or a removal of the cover endoscope 97 into or from the cover 96.

The cover endoscope 97 is constructed, as depicted in FIG. 38, of the manipulation part 12, the universal cord 13 extending from a side portion of this manipulation part 12 and an insert part 14B connected to this manipulation part 12. As shown in FIG. 38, the insert part 14B of the cover endoscope 97 is constructed of, sequentially from a proximal end of the manipulation part 12 toward its distal end, a flexible tube portion 15B, a bendable portion 16B and a hard distal end portion 17B.

The insert part 14B of the cover endoscope 97 having a small diameter is formed in a D-shape in section. Besides, the distal end portion 17B of the cover endoscope 97 is, as depicted in FIG. 35, provided with the illumination optical systems 41a, 41b and the objective optical system 42.

An outgoing end of an unillustrated light guide fiber is provided at the rear end of the illumination optical systems 41a, 41b. This light guide fiber is inserted through the insert part 14B, the manipulation part 12 and the universal cord 13.

The connector 19 is provided at the end of the universal cord 13. This connector 19 is detachably connected to the light source unit 7. Then, the illumination light emitted from the light source unit 7 is led to an incident end of the light guide fiber.

As illustrated in FIG. 34, the solid-state image sensor 20 for converting an incoming optical image into an electric signal is disposed at a rear end of the objective optical system 42. The electric signal outputted from this solid-state image sensor 20 is inputted to the video processor 8 via a signal cord 21 extending from a side portion of the connector 19 shown in FIG. 33.

As depicted in FIG. 38, the proximal end of the manipulation part 12 serves as the grasping portion 12a. The manipulation part body 12b connected to the upper side of the grasping portion 12a is provided with the angle knob 45, the air/water supply control switch 46, the suction control switch 47, the function switch 48 for photographing, etc.

The angle knob 45 is detachably attached to the manipulation part body 12b. Then, the manipulation part 12 is constructed to acquire the same manipulating feeling as that in a coverless endoscope that will hereafter be stated.

As illustrated in FIG. 33, the cover 96 with which the cover endoscope 97 is covered comprises an insert part cover section 99, the manipulation part cover section 23 and the universal cord cover section 24. The insert part cover section 99 of the cover 96 is covered on the insert part 14B of the cover endoscope 97. Further, the manipulation part cover section 23 of the cover 96 is covered on the manipulation part 12 of the cover endoscope 97 as well as on three lines of conduits that will be stated later. Besides, the universal cord cover section 24 of the cover 96 is covered on the universal cord 13 of the cover endoscope 97 as well as on three lines of conduits that will be mentioned later. Then, the cover endoscope 97 entirely fitted with the cover 96 is employed for an examination while being watertightly covered therewith.

FIG. 34 is a side sectional view showing a state where the insert part cover section 99 of the cover 96 is covered on the cover endoscope 97.

The insert part cover section 99 is intended to isolate the insert part 14B of the cover endoscope 97 from the external environment. This insert part cover section 99 is formed in an elongate shape. An endoscope manipulation part fixing mouth portion (simply called a mouth portion) 99a on the near-at-hand side and a distal end portion 99b are each formed of a hard material, e.g., a resin. Further, a mid-part between the mouth portion 99a of the insert part cover section 99 and the distal end portion 99b thereof is covered with an insert part cover sheath 99c composed of a flexible material. The insert part cover sheath 99c is formed to have a wall thickness on the order of 0.1 mm–1 mm.

Moreover, the insert part cover section 99 is internally formed with the endoscope insert channel 100 enough to insert the insert part 14B, the air supply tube 26, the water supply tube 27 and the suction tube 28.

On the side of the proximal end of the endoscope insert channel 100, the opening 25a for inserting the insert part 14B is formed in the mouth portion 99a. The endoscope insert part 14B is fitted into an opening 101 of the endoscope insert channel 100. Further, the endoscope insert channel 100 is closed at the distal end portion 99b. The insert part 14B of the cover endoscope 97 is isolated airtightly from the external environment.

In addition, the outer periphery of the insert part cover section 99 is, as illustrated in FIG. 34, formed with a fitting projection 99c externally engaging with a fitting recess 12e of the endoscope manipulation part 12.

The distal end portion 99b of the insert part cover section 99 is, as illustrated in FIG. 36, formed with a transparent window 32 in face-to-face relationship to the windows 41a, 41b and the window 42 of the endoscope at the distal end of the endoscope insert channel 100. This window 32B is formed wider than each of the illumination optical systems 41a, 41b and the objective optical system 42 of the cover endoscope 97.

Further, the distal end portion 99b of the insert part cover section 99 is formed with an air/water supply nozzle 30B opened toward the window 32B and an opening 31B as well. The air/water supply nozzle 30B connectively communicates with an opening 111 of the air supply tube 26 and an opening 112 of the water supply tube 27 in common. The opening 31B also connectively communicates with the suction tube 28.

Additionally, the air supply tube 26, the water supply tube 27 and the suction tube 28 extend from the mouth portion 99a further towards the near-at-hand side. The ends portions thereof are each opened. As depicted in FIG. 33, the air supply tube 26 connectively communicates with an unillustrated air supply source of the fluid control unit 9. Further, the water supply tube 27 connectively communicates with the air supply source via the water supply tank 33 serving as a water supply source. Still further, the suction tube 28 connectively communicates with an unillustrated suction source as well as with an unillustrated suction bottle.

As shown in FIG. 34, the treatment tool insert port 34 and the dilation tube mouth 35 are formed protrusively from the sides of the mouth portion 99a. The dilation tube mouth 35 has its internal conduit communicating with the endoscope insert channel 100. The dilation tube 36 connected to the dilator 10 is detachably connected to the dilation tube mouth 35.

The treatment tool insert port 34 protrudes backward in the axial direction of the insert part cover section 99. An internal conduit of the treatment tool insert port 34 is opened at its protruded end and communicates with the suction conduit 28 at the other end thereof. That is, the suction conduit 28 serves as a conduit of the treatment tool channel on the side of its distal end.

Cut also in the side outer periphery of the mouth portion 99a is a hold groove 99d engaging with the arm 98a of the cover holding tool 98 when holding the insert cover section 99.

the manipulation part cover section 23 and the universal cord cover section 24 of the cover 99 have the same configurations as those shown in FIGS. 8 and 9, and the explanation thereof is therefore omitted.

On the other hand, the coverless endoscope system is constructed as follows. FIG. 37 shows a configuration of the endoscope system 37 to which the coverless endoscope is connected.

The coverless endoscope 49 shown in FIG. 37 has a manipulation part 50, an insert part 51 and a universal cord 52. The manipulation part 50 is equipped with a Grasping portion 50a. A manipulation part body 50b connected to the upper side of the grasping portion 50a is provided with an angle knob 53, an air/water supply/suction control switch 54, a function switch 55 for photographing, etc.

An unillustrated treatment tool channel is formed through the coverless endoscope 49. A treatment tool insert port 151 communicating with this channel is protruded toward the proximal end of the manipulation part 50.

The universal cord 52 extends from the side portion of the manipulation part 50 having its proximal end connected to the insert part 51. The insert part 50 is constructed of, sequentially from a proximal end of the manipulation part 50 toward its distal end, a flexible tube portion 56, a bendable portion 57 and a distal end portion 58.

Further, a connector 59 is provided at the end of the universal cord 52. This connector 59 is detachably connected to the light source unit 60. The connector is at the same time connected to a video processor (VP) 62 via a cable 61 extending from the side portion thereof. Connected further to the connector 59 is a connecting tube 64 through which an unillustrated tube within the coverless endoscope 49 communicates with a fluid control unit 63.

A monitor 65 is electrically connected to the video processor 63. The monitor 65 is constructed to display an image formed by an unillustrated image sensor incorporated into in the interior of the endoscope distal end portion 58.

Note that in the illustrative example given above, the cover endoscope system and the coverless endoscope system are constructed in different ways but are not limited to the above-mentioned, The peripheral units may be employed in common. For instance, the cover endoscope system 94 is equipped with the light source unit 7, the video processor 8 and the fluid control unit 9. However, the coverless endoscope 49 can be detachably connected to the same endoscope system 94. Both in the cover endoscope and in the coverless endoscope, all the peripheral units can be used in common.

Alternatively, some of those peripheral units are usable in common both in the cover endoscope and in the coverless endoscope.

Given next is an explanation of configurations of the treatment tool insert port 134 of the cover endoscope 97 and the treatment tool insert port 151 of the insert part cover section 99.

FIG. 39 shows a state where the insert part cover section 99 is covered on the endoscope insert part 14. When the cover endoscope 97 is fitted with the insert part cover section 99 and the manipulation part cover section 23, the treatment tool insert port 134 is located substantially in the same way with the treatment tool insert port 151 of the coverless endoscope 49. More specifically, $\phi 3$, $\phi 4$ and a height with respect to the grasping portion 12a are set substantially in the same positions, wherein $\phi 3$ is an angle made by the treatment tool insert port 134 formed in the mouth portion 99a and the axial line of the endoscope 97, and $\phi 4$ is a mounting angle, i.e., the mounting position on the outer periphery of the manipulation part 12.

The treatment tool insert port 151 of the manipulation part 50 in the coverless endoscope 49 is opened at an angle $\phi 1$ (e.g., 45°) to the axial line of the insert part 51 and at an mounting angle $\phi 2$ on the outer periphery (see FIGS. 37(a) and 37(b)). The mounting angle $\phi 2$ is, as illustrated in FIG. 37(b), is approximately 30° to the right side from an UP-direction (upwards in the Figure) of the bending action. Namely, the treatment tool insert port 151 is disposed to the right side in the UP-direction. With this arrangement, the treatment tool such as a forceps can be manipulated by the right hand, thereby facilitating the insertion.

When installing the insert part of the cover endoscope 97 into the insert part cover section 99, the treatment tool insert port 134 formed in the mouth portion 99a is set at an angle $\phi 3$, e.g., about 45° made by the treatment tool insert port 134 formed in the mouth portion 99a and the axial line of the insert part 14B. Further, the manipulation part 12 is formed with an opening at an angle $\phi 4$ (e.g., 30°) to the right side in the UP-direction (see FIGS. 39(a) and 39(b)).

Note that the angles $\phi 1$, $\phi 3$ with respect to the axial line of the insert part are not limited to 45° but may include 5°~85° enough not to cause a large influence on the manipulation feeling. The same manipulation feeling is also obtained when the angles $\phi 2$, $\phi 4$ in the UP-direction range from −45° to 90°.

Further, the treatment tool insert port 134 is located in the heightwise direction and opened just under the grasping portion 12a in the same way with the coverless endoscope 49. A holding capability when inserting the treatment tool is thereby ensured.

The cover holding tool 98 shown in FIG. 40 reduces the labor for attaching and detaching the cover 90 and is disposed so as not to diffuse the adhered contaminants here and there.

The cover holding tool 98 holds, when fitting the insert part cover section 99 to the cover endoscope 97, the hold groove 99d of the insert part cover section 99 with the aid of the arm 98a branching off in two ways at its tip portion. The endoscope 97 can be thereby held without touching on the cover 96 with the hand. The operation is sanitary and thus facilitated.

The cover holding tool 98 includes a base board 98b, a support rod 98c rotatably vertically secured to this base board 98b and an arm member 98a attached to the support rod 98c. The arm member 98a branches off at its one end to hold the mouth portion 99a of the insert part cover section. Further, a hanger 98d for the cover endoscope 97 is provided at the other end of the arm member 98a. A receiving box 98e is detachably mounted on the base board 98b, whereby the trash is easily disposable.

The receiving box 98e receives the distal end portion of the endoscope when mounting the used cove endoscope 97 in the cover holding tool 98.

Note that a handle of the arm member 98a is formed relatively long so that the hanger 98d is not positioned upper the receiving box 98e.

The following is the way how the cover sections are installed on the cover endoscope 97.

Two workers—i.e., a worker A in charge of a clean area and a worker B in charge of a contaminated area-cooperate to perform the installation. At the first onset, the worker B rotates the support rod 98c to shift the arm member 98c from an upper position of the receiving box 98e.

Next, the worker A wears a sterilized glove and removes the insert part cover section 99 out of an unillustrated package. The hold groove 99d is engaged with the forked portion of the arm member 98a, whereby the insert part cover section 99 is held by the holding tool 98. Subsequently, the worker B connects the dilation tube to the dilation tube mouth 35 to dilate the endoscope insert channel 100. In this state, the worker B inserts the insert part 14B of the cover endoscope 97 into the opening 101, thus installing the insert part 14B into the insert part cover section 99.

The arrangement of the conduits 26, 27, 28 each extending from the mouth portion 92a is the same as that in the first embodiment. The angle knob 45 is attached the same. The manipulation part cover section 23 and the universal cord cover section 24 are installed also in the same manner. Their explanation is therefore omitted.

The worker B connects the air supply conduit 26, the water supply conduit 27 and the suction conduit 28 to the fluid control unit 9, thus finishing the installation of the endoscope cover.

Next, the removal of the cover sections will be explained.

The cover sections are removed after finishing the examination. To begin with, the worker moves the arm member 98a of the cover holding tool 98 to a position above the receiving box 98e. Subsequently, the cable 21 is detached from the connector 19. Further, the air supply conduit 26, the water supply conduit 27 and the suction conduit 28 are removed from the fluid control unit 9. Moreover, the connector 19 is pulled out of the light source unit 7. The hold groove 99d is engaged with the arm member 98a. The dilation tube 36 is attached to the dilation tube mouth 35. Next, the universal cord cover section 24 is removed, and the angle knob 45 is detached from the manipulation part body 12b.

Thereafter, the manipulation part cover section 23 is exfoliated, and the insert part 14B of the cover endoscope 97 is pulled out of the insert part cover section 99 afterward. the thus removed cover endoscope 97 is caught by the hanger 98d. The insert part cover section 99 is taken off the arm member 98a and thrown into the receiving box 98e. The removal of the cover is thus completed. The receiving box 98e is located just under the forked portion of the arm member 98a. This arrangement eliminates the necessity for bringing the contaminated cover sections to the receiving box 98e. The contaminants as a source of the contamination are not diffused to the surroundings. The operation is therefore sanitary.

The cover holding tool may be constructed as shown in FIG. 41.

A cover holding tool 121 illustrated in FIG. 41 is constructed so as not to diffuse the contaminants to the surroundings. The cover holding tool 121 is also contrived to adhere no contaminant to a working wear like a white robe of the worker.

A housing box 135 shown in FIG. 41 has s stretchable cover 136. The stretchable cover 136 taking a double structure consists of, e.g., a commercially available bag 137 and an external frame member 138. Configurations of others are the same as those in the cover holding tool shown in FIG. 40, and they are marked with the like symbols with an omission of the explanation thereof.

The following is the way how the cover 96 is removed by use of the cover holding tool 121. Note that the procedures of installing the cover are the same as those stated before, and the description is also omitted.

When finishing the examination, the worker at first extends the arm member 98a of the cover holding tool 121 up to a position above the housing box 135. The hold groove 99d of the cover is engaged with the formed portion of the arm member 98a. Then, the stretchable cover 136 is raised in close proximity to the mouth portion 99a. Next, the cable 21 is detached from the connector 19. Further, the air supply conduit 26, the water supply conduit 27 and the suction conduit 28 are removed from the fluid control unit 9. Moreover, the connector 19 is detached out of the light source unit 7. The dilation tube 36 is dilated and attached to the dilation tube mouth 35.

Next, the universal cord section 24 is removed and thrown into the housing box 135. The angle knob 45 is detached from the manipulation part body 12b. The manipulation part cover section 23 and the like are exfoliated and then thrown into the housing box 135.

The insert part 14B of the cover endoscope 97 is pulled out of the insert part cover section 99 dilated. The cover endoscope 97 pulled out is caught by the hanger 98d. Further, the insert part cover section 99 is taken off the arm member 98a and thrown into the housing box 135. Thus, the removal of the cover is completed.

The housing box 135 is disposed just under the arm member 98a, and the stretchable cover 136 is also prepared. With this arrangement, there is no possibility to contaminate the working wear during the embracement of the insert part cover section 99 and the removal of the cover. Hence, the contaminants are not diffused to the surroundings. The working wear does not become an infectious medium. The cover can be sanitarily abandoned. Note that pry housing box 55 may be used in common to the package 81 shown in FIG. 17.

In accordance with this embodiment, the treatment tool insert port of the coverless endoscope is disposed in the same way with the treatment tool insert port of the cover endoscope. The operator does not therefore have an unfitted feeling during the manipulation. Besides, during the treatment, the operator does not have to shift the treatment tool insert port with a twist of the left hand to the UP-side, especially, to the right hand. It is possible to prevent an oversight of the aiming diseased part and a damage to the somatic cavity wall due to a movement of the distal end portion.

FIGS. 42 through 44 show a fifth embodiment of the present invention. FIG. 42 is a view showing a configuration of the distal end portion of the insert part cover section. FIG. 43 is an explanatory view showing an operation of the cover type endoscope unit. FIG. 44 is an explanatory view showing an aiming action in the cover type endoscope unit.

FIG. 42(a) illustrates a distal end portion 121 of an insert part cover section 120 for side viewing. FIG. 42(b) is a sectional view taken along the line B—B of FIG. 42(a).

The insert part cover section 120 and the distal end portion 121 shown in FIG. 42(a) are each formed of a soft resin. The distal end portion 121 is provided with an elastic member for giving a bendability beforehand.

A window 122 composed of a transparent and flexible material, e.g., a resin, is formed in the outer peripheral surface of the distal end portion 121 in the vicinity of its tip. The window 122 having a wall thickness of approximately 0.3~2 mm is formed in a remarkably wide range in the peripheral direction as well as in the axial direction of the insert part of the cover section.

Further, an endoscope insert channel 123 passes through the insert part cover section 120 in the axial direction thereof. A cover endoscope which will be mentioned later is inserted into this endoscope insert channel 123.

FIGS. 43(a) and 43(b) are sectional views each showing a state where an endoscope insert part 124 is inserted into the endoscope channel 123 of the insert part cover section 120. The cover endoscope employed herein includes a view optical system 125 having a visual field in the direction substantially orthogonal to the axial direction of the insert part thereof. An image sensor 126 is disposed in rear of the view optical system 125. Namely, the cover endoscope in this embodiment is of a side view type.

A suction conduit 127 serving as a forceps channel extends in the axial direction in the insert part cover section 120. A bendable leaf spring 129 is provided downwardly of the suction conduit 127. The endoscope manipulation part fixing mouth portion formed at the proximal end of the insert part cover section 120 is common to that in the fourth embodiment, and the explanation is therefore omitted.

Herein, a rise-up mechanism of the cover type endoscope unit will be explained.

When the insert part cover section 120 is pulled in toward the endoscope manipulation part, as illustrated in FIG. 43(b), the endoscope insert part 124 is inserted up to the vicinity of the distal end of the endoscope insert channel 123. At this time, the insert part cover section 120 assumes a rectilinear shape, resisting the reaction of the lead spring 129. When the insert part cover section 120 is moved away from the endoscope manipulation part, the distal end portion 121 gets free.. For this reason, as illustrated in FIG. 43(a), the insert part cover section 120 is bent because of the bendability of the leaf spring 129. A suction channel 127 rises up, whereby the cannulation or the like becomes practicable.

According to the rise-up mechanism for a disposal sheath, as disclosed in U.S. Pat. No. 4,646,722, the channel fixed to the sheath has hitherto been forcibly pushed up by a rise-up board provided on the side of the endoscope. For this reason, a wire for pulling the rise-up board is stretched out, with the result that a predetermined rise-up angle is not obtained, or the wire is often broken.

In contrast with this, this embodiment does not involve the use of the wire. The rise-up is attained with to-and-fro movements of the insert part cover section. The endoscope is not therefore broken down, and the safety rise-up can be effected at the predetermined angle (approximately 0°~90°).

Further, in accordance with this embodiment, as shown in FIG. 44, a papilla 130 is opened obliquely on the occasion of the cannulation, a cannula 128 does not match in its advancing direction due to a vertical rise-up as seen in the prior art. An insertion into a bile duct or pancreatic duct is difficult in some cases. Contrastingly in this embodiment, the insert part cover section 120 is rotatable, and a sideway rise-up can be also attained. An aiming performance of the cannulation can be improved.

Note that the resent invention is not limited to the electronic endoscope but may be applied to, e.g., optical fiber endoscopes and ultrasonic endoscopes.

It is apparent that, in this invention, a wide range of different working modes can be formed based on the invention without deviating from the spirit and scope of the invention. This invention is not restricted by its specific working modes except being limited by the appended claims.

What is claimed is:

1. An endoscope system comprising:

a cover endoscope fittable with an endoscope cover and used by covering its outer surface with said endoscope cover; and a coverless endoscope used without being covered with said endoscope cover;

wherein each of said cover endoscope and said coverless endoscope includes an objective optical system provided at a distal end of an insert part, an eyepiece optical system capable of viewing directly with the naked eye and a mask signal generation means, interposed between said objective optical system and said eyepiece optical system, for masking a part of a range of visual field obtained by said objective optical system, a mask configuration by said mask signal generation means for the range of visual field of said objective optical system in said cover endoscope is substantially the same as that in said coverless endoscope, and the ranges of visual fields capable of viewing in said respective eyepiece portions are substantially the same.

2. An endoscope system comprising:

a cover endoscope fittable with an endoscope cover and used by covering its outer surface with said endoscope cover; and a coverless endoscope used without being covered with said endoscope cover;

wherein an objective optical system capable of viewing a subject is disposed at the distal end of an insert part of each of said cover endoscope and said coverless endoscope, said endoscope cover is formed with a window in a face-to-face relationship to said objective optical system, and a ray height of a first incident surface of said objective optical system of said cover endoscope is set smaller than a ray height of a first incident surface of said objective optical system of said coverless endoscope.

3. An endoscope system comprising:

a cover endoscope fittable with an endoscope cover and used by covering its outer surface with said endoscope cover; and a coverless endoscope used without being covered with said endoscope cover;

an imaging means, provided at the distal end of the insert part of each of said cover endoscope and said coverless endoscope, for converting a subject image into an electric signal and a display means for displaying the subject image imaged by said imaging means in the form of an endoscope image, said screen being a screen of said display means, said endoscope image displayed by said display means and obtained by said cover endoscope being substantially the same as said endoscope image displayed by said display means and obtained by said coverless endoscope on said screen of said display means; and further comprising a mask signal generation means for masking a part of said endoscope image obtained by said cover endoscope and a mask signal generation means for masking a part of said endoscope image obtained by said coverless endoscope, said mask signal generation means effecting masking so that the display ranges of said respective endoscope images are substantially the same on the screen of said display means.

4. The endoscope system according to claim 2, wherein an aperture of a first entrance pupil in said objective optical system of said cover endoscope is set smaller than an aperture of a second entrance pupil in said objective optical system of said coverless endoscope to reduce the ray height of said first incident surface.

5. The endoscope system according to claim 3, wherein each of said mask means electrically performs masking on the electric signal outputted said imaging means of each of said endoscopes.

* * * * *